United States Patent [19]

Wissner et al.

[11] 4,202,988
[45] May 13, 1980

[54] PROSTENOIC ACIDS AND ESTERS

[75] Inventors: Allan Wissner, Monsey, N.Y.; Martin J. Weiss, Oradell; Karel F. Bernady, South Sommerville, both of N.J.

[73] Assignee: American Cyanamid Company, Stamford, Conn.

[21] Appl. No.: 782,851

[22] Filed: Mar. 30, 1977

[51] Int. Cl.$^2$ ............................................ C07C 177/00
[52] U.S. Cl. ............................ 560/118; 260/410.9 R; 260/413; 260/429.7; 260/438.1; 260/464; 260/465 D; 560/53; 560/231; 562/463; 562/500; 424/304; 424/305; 424/308; 424/317; 556/428; 556/482; 556/485; 556/442; 556/441; 556/416; 556/427; 556/471; 556/476

[58] Field of Search ........................... 560/121, 118; 260/514 D, 410.9 R, 413; 562/500

[56] References Cited
PUBLICATIONS

Samuelsson, "Advances in Prostaglandin and Thromboxane Research," pp. 484–491 (1976).

Primary Examiner—Robert Gerstl
Attorney, Agent, or Firm—Richard J. Hammond

[57] ABSTRACT

This disclosure describes derivatives, analogs, and congeners of prostanoic acid having a terminal cyclic moiety in the β-chain which possess the pharmacological activities associated with the prostaglandins.

47 Claims, No Drawings

PROSTENOIC ACIDS AND ESTERS

BACKGROUND OF THE INVENTION

Applicants are not aware of any prior art reference which, in their respective judgments as one skilled in the prostaglandin art, would anticipate or render obvious the novel compounds of the instant invention; however, for the purpose of fully developing the background of the invention and establishing the state of the requisite art, the following references are set forth: U.S. Pat. No. 3,884,969; Japanese Pat. No. 3,884,969; German Offen. No. 2,515,770; German Offen. No. 2,510,818; and Netherlands published Patent Application No. 7,410-185.

BRIEF SUMMARY OF THE INVENTION

This invention relates to novel prostenoic acids and esters of the formula:

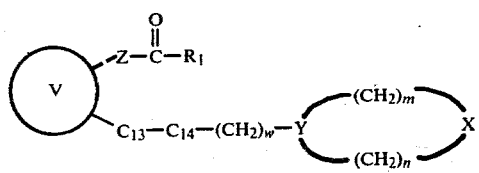

wherein V is selected from the group consisting of

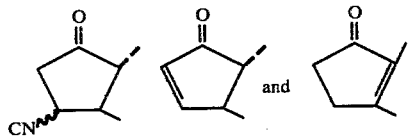

$R_1$ is selected from the group consisting of hydroxy, triloweralkylsilyloxy ($C_1$ to $C_4$) and straight or branched chain alkoxy ($C_1$ to $C_6$); Y is a trivalent radical selected from the group consisting of

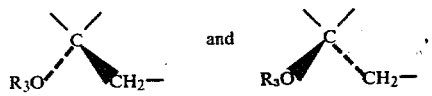

wherein $R_3$ is selected from the group comprising hydrogen, triloweralkylsilyl and alkanoyl ($C_2$ to $C_5$); X is a divalent radical selected from the group comprising

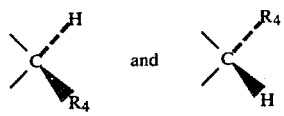

wherein $R_4$ is selected from the group consisting of a branched or straight chain alkyl group ($C_1$ to $C_7$), hydrogen, phenoxy and phenoxy substituted with a compound selected from the group consisting of halogen, trifluoromethyl, and methoxy; n is zero or an integer from 1 to 4; m is zero or an integer from 1 to 4; the sum of n and m has the value of 2 to 4; the moiety $C_{13}$–$C_{14}$ is ethylene or trans vinylene; w is 1 or zero, Z is a divalent radical selected from the group consisting of —$(CH_2)_p$—,

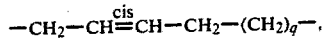

—$(CH_2)_t$—O—$CH_2$— and —$(CH_2)_t$—S—$CH_2$— wherein p is an integer from 5 to 7, q is an integer from 1 to 3, t is an integer from 3 to 5.

DETAILED DESCRIPTION OF THE INVENTION

Useful pharmacologically acceptable salts of the above formula wherein $R_1$ is hydroxy are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the aliphatic, cycloliphatic, and araliphatic amines containing up to an including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic solutions are preferred. For that purpose, it is preferred because of increased water solubility that $R_1$ be hydrogen or a pharmacologically acceptable cation. For subcutaneous or intramuscular injection, sterile solutions or suspensions of the acid, salt, or ester formed in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstrom, et al., J. Biol. Chem., 238, 3555 (1963) and Horton, Experientia, 21, 113 (1965) and references cited therein. All of the so-called natural prostaglandins are derivatives of prostanoic acid:

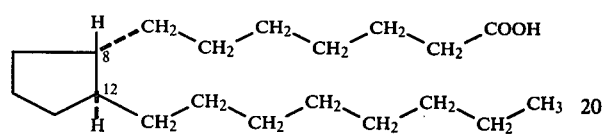

The hydrogen atoms attached to C-8 and C-12 are in trans-configuration. The natural prostaglandins represent only one of the possible optical isomers. The compounds of this invention include all possible optical isomers.

The compounds of this invention which have the structure as shown in formula (A) wherein R, Z, $R_2$, R, m, n, w and x are as herein above defined are said to be in the same configuration as the natural prostaglandins with respect to the configurations at $C_8$ and $C_{12}$ and are designated by the prefix nat. The enantiomer, represented by formula (B) is said to be in the mirror image or ent configuration. A cyano group at $C_{11}$ drawn with a dotted line ($C_{11}$---$C_N$) is said to have an α configuration; a solid line ($C_{11}$—CN) indicated a β configuration. The configuration at Y and X will be expressed in terms of R and S as is understood in the art. For example, the compound represented by formula (C) is named: nat-15S,16S-15-dihydroxy-9-oxo-15,16-trimethylene-13-trans-10-prostadienoic acid; its enantiomer (formula D) is named ent-15R,16R-15-dihydroxy-9-oxo-15,16-trimethylene-13-trans-10-prostadienoic acid. The racemate [1:1 mixture of (C) and (D)] is named nat-15S,16S-(and ent-15R,16R)15-dihydroxy-9-oxo-15,16-trimethylene-13-trans-10-prostadienoic acid. In a similar manner, the compounds represented by formulae (E) to (J) have the configurations shown below.

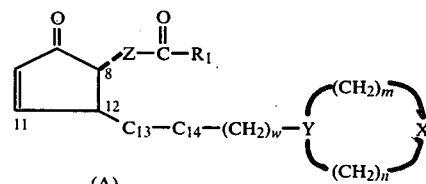

(A)

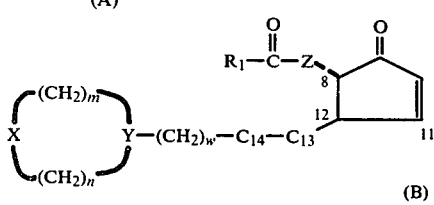

(B)

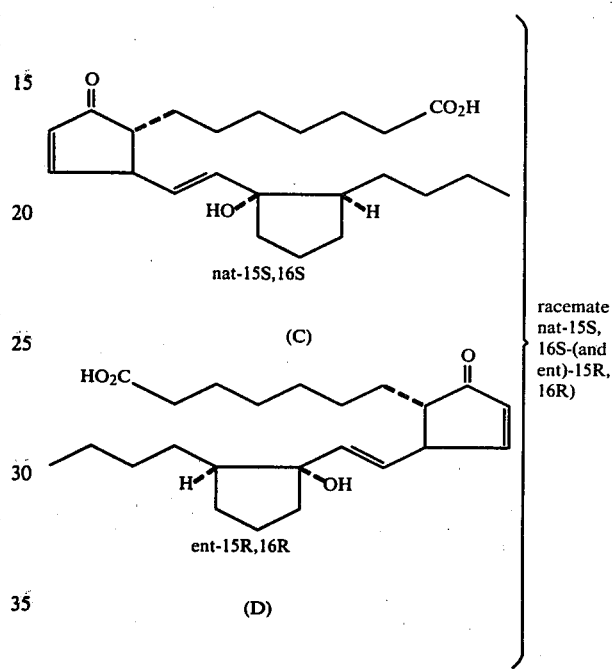

racemate nat-15S, 16S-(and ent)-15R, 16R)

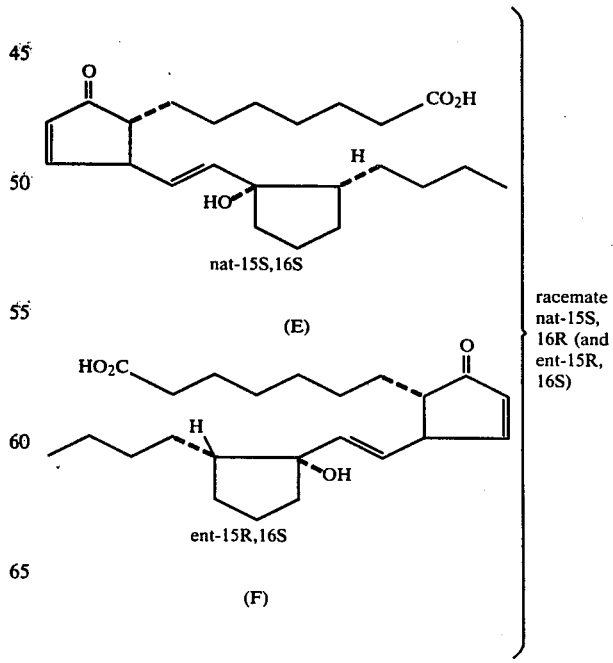

racemate nat-15S, 16R (and ent-15R, 16S)

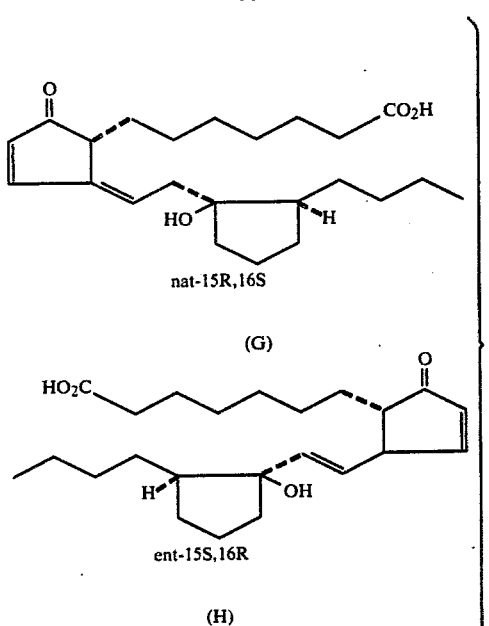

(G)

(H)

racemate nat-15R, 16S-(and ent-15S, 16R)

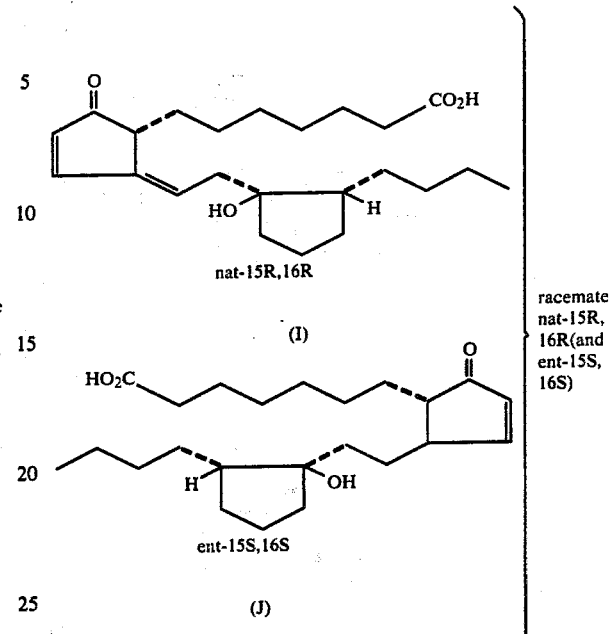

(I)

(J)

racemate nat-15R, 16R(and ent-15S, 16S)

The novel compounds of this invention can be prepared by the reaction sequences illustrated in Flowsheet A below, wherein n, m, X, w and Z are as hereinabove defined; $R_1'$ is straight or branched-chain alkoxy ($C_1$ to $C_{12}$) or triloweralkylsilyloxy ($C_1$ to $C_4$); $R_2'$ is triloweralkylsilyloxy ($C_1$ to $C_4$) or alkanoyloxy ($C_2$ to $C_5$); $R_1''$ and $R_2''$ are hydroxy.

Flowsheet A

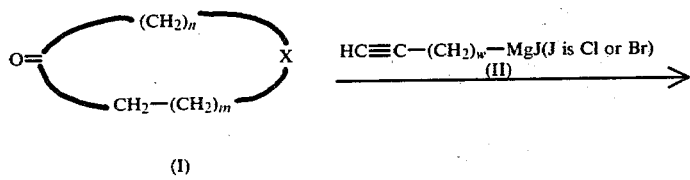

-continued
Flowsheet A
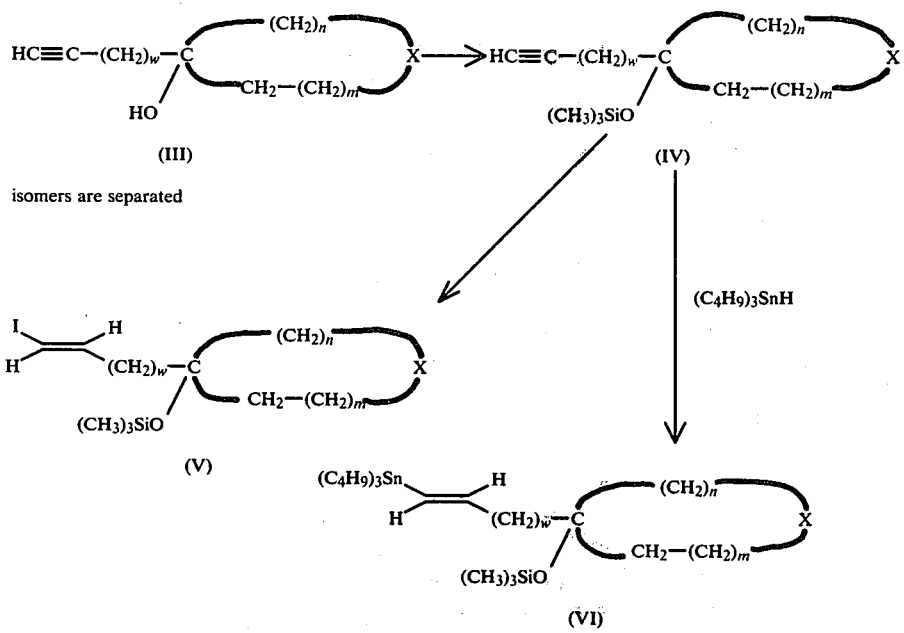
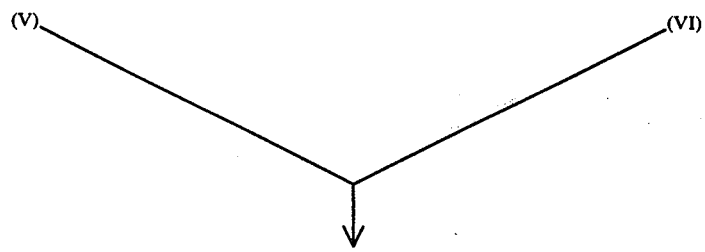
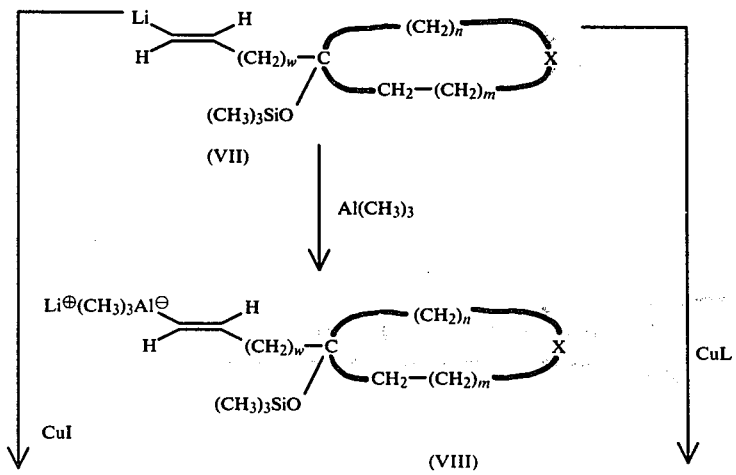

-continued
Flowsheet A
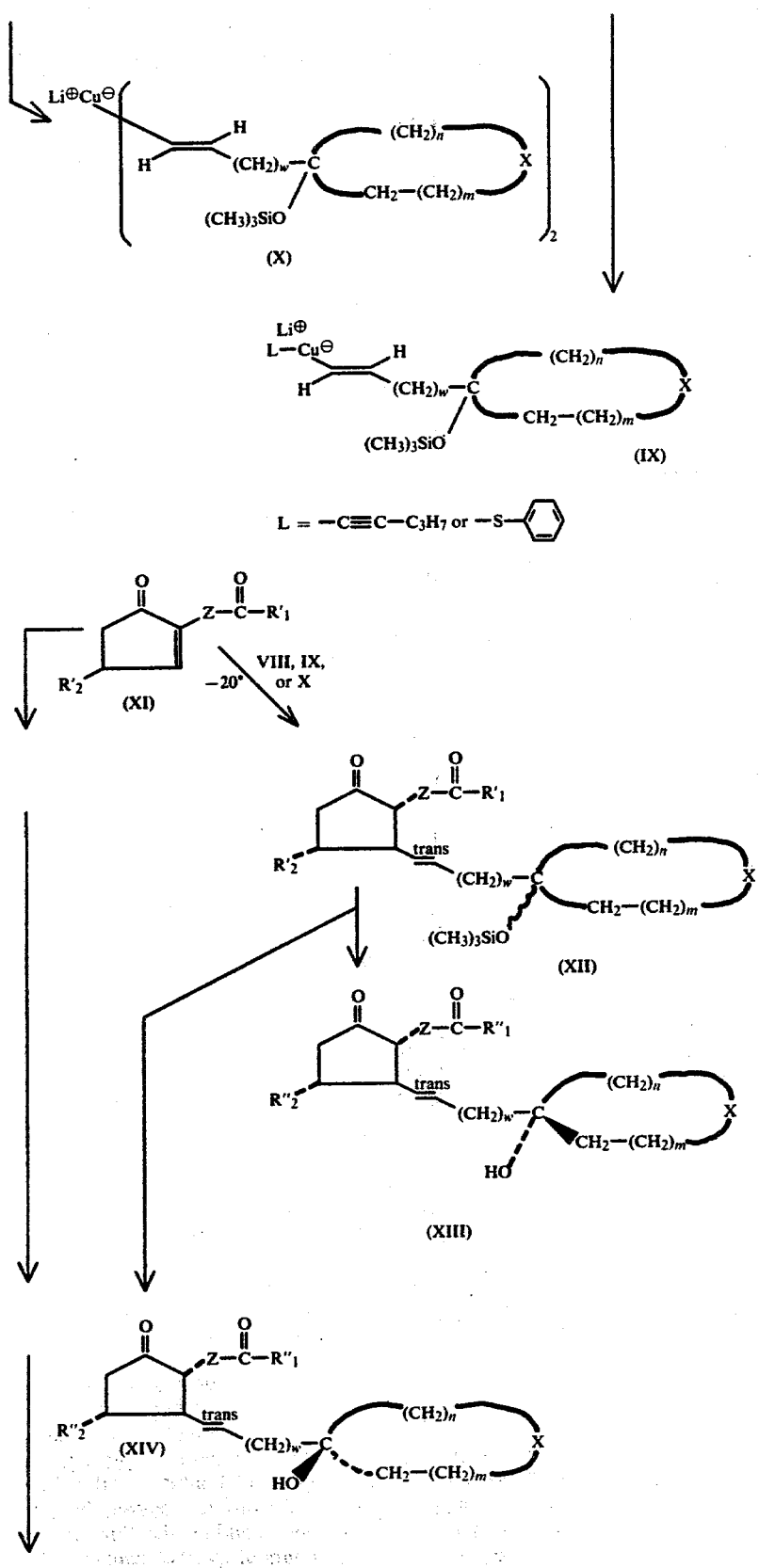

Flowsheet A -continued

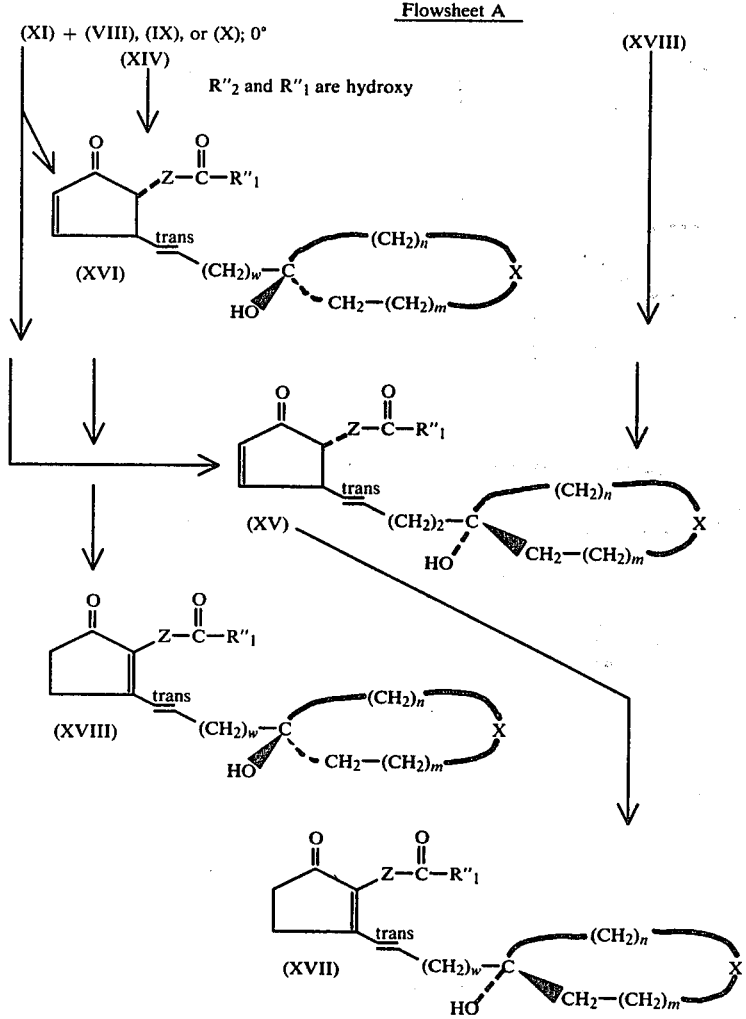

In accordance with the scheme as outlined hereinabove in Flowsheet A a ketone (I) is reacted with a Grignard reagent (II) such as acetylene magnesium chloride (II, w=0) or propargyl magnesium bromide (II, w=1) to give the acetylenic alcohols (III). In those cases where X is not —$CH_2$— two isomeric acetylenic alcohols are formed. These isomers can be separated by procedures well known to the art including fractional crystallization, fractional distillation and various chromatographic procedures. The individual isomers can then be carried through the remaining reactions outlined in Flowsheet A.

The acetylenic alcohol (III) is converted to its trimethylsilyl ether in the usual manner. The silylated derivative (IV) is then treated with diisoamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-trans-1-alkene (V).

The vinyl iodide (V) is converted to the trans-vinyl lithium derivative (VII) with clean retention of configuration by treatment at about −78° C. in hexane or toluene solution with either one equivalent of n-butyl lithium or two equivalents of t-butyl lithium. It is preferable for this treatment to proceed for about one hour at −78° C., then for about one hour at −40° C. and finally for about one hour at about 0° C. For the subsequent preparation of lithio alanate reagents (VIII) it is preferable to use n-butyl lithium, and for the lithio cuprate reagents (IX) or (X) t-butyl lithium is the agent of choice. The same vinyl lithium derivative (VII) can be prepared from the 1-tri-n-butylstannyl 3- trimethylsilyloxy-trans-1-alkene (VI) by treatment of (VI) with n-butyl lithium in hexane solution at −40° to 0° C. (VI) in turn is readily prepared by the addition of tri-n-butyl tin hydride to the acetylene (IV) in the presence of bisazoisobutyronitrile followed by vacuum distillation at a high enough temperature (about 170° C.) to isomerize any of the cis-vinyl tin compound to the trans-vinyl tin compound.

For the preparation of the alanate reagent (VIII) or the like, a molar equivalent of a tri-lower alkyl (1–5 carbon atoms) aluminum (e.g., trimethyl aluminum), dissolved in a solvent such as hexane, is added to the vinyl lithium derivative (VII) at about 0° C. After about 15–45 minutes at this temperature the requisite blocked cyclopentenone (XI) is added and the reaction mixture is stirred for about 18 hours at ambient temperatures.

The mixture is quenched with aqueous hydrochloric acid in the cold and the product is obtained by extraction. In the 11-deoxy series the blocking trialkylsilyl group is removed on treatment with acetic acid: tetrahydrofuran:water (4:2:1) at room temperatures for about twenty minutes. The ester group can then be saponified in the usual manner. In the 11-oxy series, the silyl groups are removed by treatment with acetic acid:-water:tetrahydrofuran (20:10:3) at about 40° C. for about 4 hours. Alkyl esters of the 11-oxy series are not disturbed by this treatment and cannot be saponified by chemical means in view of the instability of the 11-hydroxy-9-ketone to base treatment. However, the ester can be cleaved by treatment with Baker's Yeast, a procedure well-known in the art.

For the preparation of the asymmetrical lithio cuprate (IX) or the like, a solution of one molar equivalent of copper (I)-1-alkyne, preferably copper (I)-1-pentyne, in anhydrous hexamethylphosphorous triamide, preferably three to five molar equivalents, and anhydrous ether is added to one molar equivalent of the aforementioned vinyl lithium (VII) solution cooled to about −78° C. The solution is then stirred for about one hour at −78° C. A cuprate reagent containing a p-thiophenoxide ligand

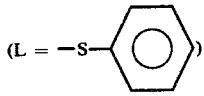

can also be used; it is prepared by first forming lithium thiophenoxide by adding an equivalent of n-butyl lithium in hexane to an etheral solution of thiophenol. To this is then added a solution of one equivalent of tri-n-butyl phosphine copper iodide complex in ether. The resulting solution of phenylthio copper is added at −78° C. under inert gas to the solution of the vinyl lithium compound (VII). The mixture is then maintained at −78° C. for one hour. To either of these cuprate solutions at −78° C. a molar equivalent of the requisite cyclopentenone (XI) is added. After several hours at −20° C. the reaction mixture is quenched with aqueous ammonium chloride solution and the blocked product (XII) is isolated in the usual manner. The deblocking of this product is then carried out in the manner as described hereinabove.

The products are finally purified by chromatographic procedures in the usual manner.

In those cases where X is not $CH_2$ and m≠n−1, two isomers are formed which differ in the configuration at $C_{15}$ or $C_{16}$; both isomers are racemates and they can be separated from each other by chromatographic procedures well known in the art.

For the preparation of the symmetrical lithion cuprate (X) one molar equivalent of copper (I) iodide tributylphosphine complex, dissolved in anhydrous ether, is added at about −78° C. to two molar equivalents of the aforementioned vinyl lithium (VII) solution in hexanes, cooled to −78° C. After about one hour at this temperature, the lithio cuprate (X) is treated with the requisite cyclopentenone (XI) as des cribed hereinabove for the conjugate addition with the 1-alkynyl lithio cuprate (IX).

In order to ensure a trans-relationship in (XII), (XIV) or (XIII), these products can be submitted to conditions known in the literature to equilibrate cis 8-iso-$PGE_1$ to a mixture contaning about 90% of the trans-product [see E. G. Daniels, et al., *J. A. C. S.*, 90, 5894 (1968)].

These conditions involve treatment with potassium acetate in aqueous methanol for about 96 hours at room temperature. The cis and trans products are separable by chromatographic procedures.

Most of the cyclopentenones required for the purposes of this invention have been described in the literature or can be prepared by procedures quite analogous to those already described. Appropriate references are provided in the examples which follow. The synthesis of certain nonreference requisite cyclopentenones is also described therein.

Treatment of the 11-hydroxy derivatives represented by formulae (XIV) or (XIII) in which $R_2''$ is hydroxy with dilute acid results in dehydration of the β-ketol system and the formation of the corresponding $\Delta^{10}$ derivatives (XVI) or (XV) (prostaglandins of the A type). A preferred procedure involves treatment in tetrahydrofuran:water (2:1) solvent 0.5N in hydrochloric acid for about twenty hours at ambient temperatures. Under these conditions tetrahydropyranyl or trialkylsilyl esters undergo hydrolysis if this procedure is applied to the initial conjugate addition product (XII). More prolonged treatment with acid or preferably treatment with dilute base, e.g., sodium carbonate in aqueous methanol or an amine such as piperidine, effects the conversion of (XIV) or (XIII) to the $\Delta^{8(12)}$ derivatives (XVIII) or (XVII) (prostaglandins of the B type). The $\Delta^{10}$ derivatives (XVI) and (XV) can also be prepared by preforming a conjugated addition of cuprate (IX) (L=—C≡$CC_3$ $H_7$) to the cyclopentenone (XI) ($R_2$ 40 is trimethylsilyloxy) as described herein above and allowing the resulting solution to reach a temperature of 0° C. for 1-2 hours. Under these conditions, both conjugate addition and elimination of the $C_{11}$ trimethylsilyloxy group occurs; after deblocking as described hereinabove, the $\Delta^{10}$ derivatives (XVI) and (XV) are isolated and separated by chromatographic procedures.

The 13-dihydro derivatives ($C_{13}$–$C_{14}$ is ethylene) of this invention can be prepared by reduction of the $\Delta^{13}$ function in the corresponding 13-prostenoic acids or esters.

Compounds of this invention which contain a cyano group at $C_{11}$ are prepared by reacting the corresponding $\Delta^{10}$ derivative with acetone cyanohydrin and a base catalyst such as sodium carbonate.

The prostanoic and prostenoic carboxylic acids of this invention are convertible to the corresponding alkyl esters by treatment with the appropriate diazoalkane in the usual manner. The preparation of diazoalkanes by various procedures are well-described in the art, see for example C. D. Gutsche, *Organic Reactions*, VIII, 389 (1954). Certain of the esters of this invention can also be obtained directly by use of the appropriate cyclopentenone ester (see XI). The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydride is then treated with the appropriate alcohol to give the derivatized product. [For a pertinent literature analogy see *Prostaglandins,* 4, 738 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy see U. S. Patent 3,821,279, June 28, 1974). A third procedure involves use of dicyclohexylcarbodiimide in the usual manner; for a pertinent literature analogy see German Offen. 2,365,205 (July 11, 1974); *Chem. Abst.,* 81, 120098 g. (1974).

Certain of the ketones (I) of this invention are prepared as indicated in Flowsheet B below:

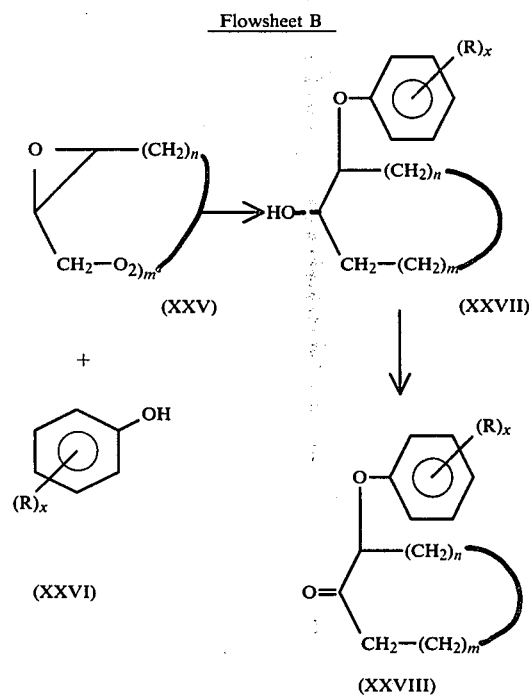

(XXV) (XXVII)

+

(XXVI)

(XXVIII)

wherein n and m are as hereinabove defined and the moiety

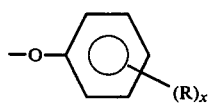

represents a phenoxy group which is optionally substituted with one or more halogen, trifluoromethyl, and lower alkyloxy ($C_1$ to $C_4$) groups.

As indicated in Flowsheet B the reaction of an epoxide (XXV) with a substituted or unsubstituted phenol (XXVI) in the presence of a catalytic amount of aqueous sodium hydroxide and a phase transfer catalyst such as methyl tricapryly ammonium chloride and the like at 70° -80° C. gives the phenoxy substituted alcohol (XXVII) which in turn is oxidized with an oxidizing reagent such as pyridinium chlorochromate in methylene chloride to give the phenoxy substituted ketone (XXVIII).

The other ketones (I) used in this invention are known in the literature or can be made by procedures well known to the art [G. Lardeli, U. Lamberti, W. T. Walles and A. P. de Jonge, *Rec. Trav. Chem. Pays-Bas,* 86 481 (1976); Ng. Ph. Buu-Hoi, T. B. Loc and Ng. Dat Xuong., *Bull. Soc. Chem. France,* 174 (1958); and G. H. Posner, *Organic Reactions,* 19, 1 (1972)].

Also embraced within the scope of this invention are the various intermediates, the use of which is described herein. These are represented by the following generic formulae (K) and (L).

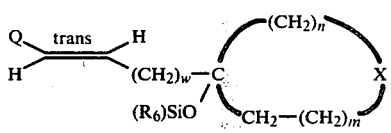

(K)

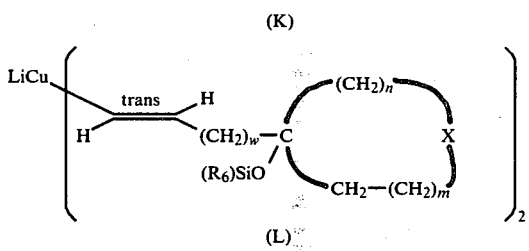

(L)

Wherein w, n, m and X are as hereinabove defined; $R_6$ is lower alkyl ($C_1$ to $C_6$); Q is iodine, triloweralkyl ($C_1$-$C_6$) tin, lithium,

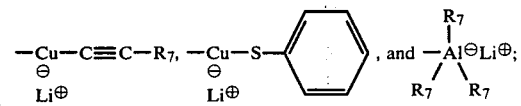

$R_7$ is lower alkyl ($C_1$-$C_7$).

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatography including recycling techniques. [See G. Fallick, *American Laboratory,* 19–27 (August, 1973) as well as references cited therein. Additional information concerning high speed liquid chromatography and the instruments necessary for its application is available from Waters Associate, Inc., Maple Street, Milford, Mass.]

It is also possible to prepare the individual enantiomers in the 11-oxy series via the conjugate addition procedure discussed above by starting with a resolved 4-oxycyclopentenone [see (XI), $R_2'$ is tri-loweralkylsilyloxy]. The resulting products (XIV) and (XIII) after deblocking as described hereinabove are obtained in their optically active forms.

The 4-hydroxycyclopentenone racemates may be resolved into their component enantiomers (XXXI) and (XXXII) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-v-methylpentanoic acid hydrochloride [to give (XXXIII)], (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (XXXI) and (XXXII). A useful procedure for the resolution of a 4-hydroxycyclopentenone racemate via an oxime such as (XXXIII) is described in the art [R. Pappo, P. Collins and C. Jung, *Tetrahedron Letters*, 943 (1973)].

deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih, et al, *J. A. C. S.*, 95, 1676 (1973); J. B. Heather, et al., *Tetrahedron Letters*, 2213 (1973); R. Pappo and P. W. Collins, *Tetrahedron Letters*, 2627 (1972); and R. Papo, P. Collins, and C. Jung, *Ann. N. Y. Acad. Sci.*, 180, 64 (1974). For a description of the baker's yeast procedure see C. J. Sih, et al. *J. A. C. S.*, 94, 3643 (1972).

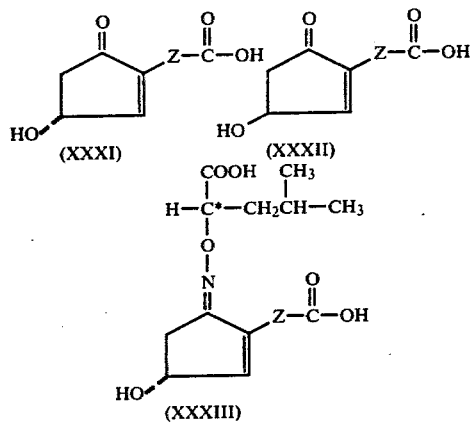

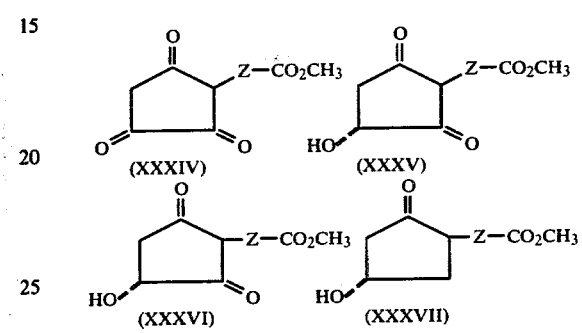

An alternative procedure for the preparation of the 4(R)-hydroxycyclopentenone enantiomers such as (XXXI) involves as a key step the selective microbiological or chemical reduction of trione (XXXIV) to the 4(R)-hydroxycyclopentanedione (XXXV). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine)rhodium (I) tetrafluoroborate in the presence of one equivalent of organic base, such as triethylamine.

Conversion of hydroxycyclopentanedione (XXXV) to an enol ether or enol ester, (XXXVI, E=alkyl, preferably iso-propyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride in a non-protropic solvent at a temperature of about −10° to −15° C. Reduction of (XXXVI) with excess sodium bis(2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (XXXVII). The ester (XXXVII), after blocking the hydroxy function as described hereinabove, can be subjected to conjugate addition reactions also as described hereinabove. The conjugate addition product, after Procedures for the preparation of the requisite cyclopentanetriones (XXXIV) are well-established in the art and generally involve the treatment of an -1 oxo long chain ester (XXXVIII) with methyl or ethyl oxalate and a base such as sodium methoxide in methanol, followed by treatment with dilute hydrochloric acid in aqueous methanol to effect the dealkoxalylation of the intermediate (XXXIX). See J. Kutsube and M. Matsui, *Agr. Biol. Chem.*, 33 1078 (1969); P. Collins, C. J. Jung and R. Pappo, *Israel Journal of Chemistry*, 6, 839 (1968); R. Pappo, P. Collins and C. Jung, *Ann. N. Y. Acad. Sci.*, 180, 64 (1971); C. J. Sih, et al., *J. A. C. S.*, 95, 1676 (1973) (see reference 7); and J. B. Heather, et al., *Tetrahedron Letters*, 2313 (1973) for pertinent background literature.

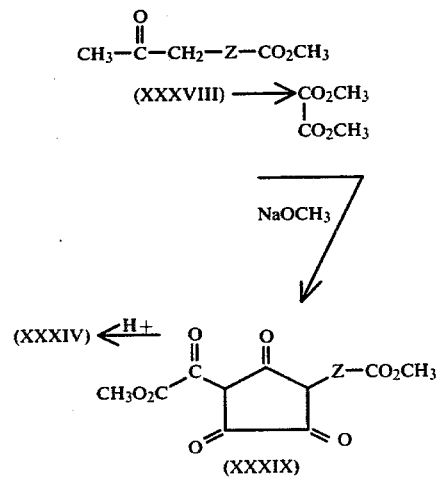

The intermediate keto esters (XXXVIII) may be prepared by a variety of methods known to the art. One useful procedure is outlined below and involves alkylation of ethyl acetoacetate sodium salt (XL) in the usual manner with the appropriate side-chain precursor (XLI, X=Cl, Br, I, preferably Br or I) followed by decarbethoxylation and reesterification, all in the usual manner.

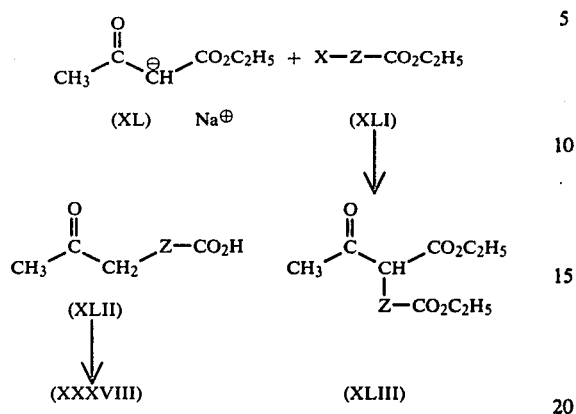

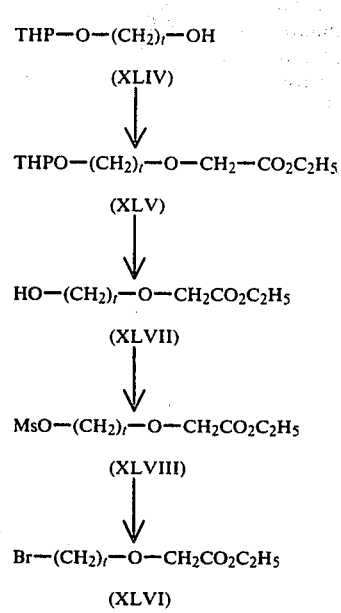

The side-chain precursors (XLI) are commercially available where Z is —(CH$_2$)$_p$—, and can be prepared as described in Belgian Pat. No. 786,215 (granted and opened to inspection Jan. 15, 1973).

Those precursors wherein Z is —(CH$_2$)$_r$—O—CH$_2$— can be prepared by the transformation shown directly below starting with the mono-tetrahydropyranyl derivative (XLIV). Thus, (XLIV) is converted to the lithium alcoholate by treatment with butyl lithium, the alcoholate is then O-alkylated with ethyl bromoacetate to provide (XLV), which on de-O-tetrahydropyranylation, mesylation and reaction with lithium bromide gives the required (XLVI). (These and all the above-described transformations can be effected in the usual manner, well-established in the art; pertinent examples for most of the reactions can be found in the above-cited Belgian Pat. No. 786,215.)

It is also possible to resolve the 4-hydroxycyclopentenone racemate (XLIX) by microbiological means. Thus, treatment of the 4O-alkanoyl or aroyl derivatives (L, R$_{18}$=aryl or alkyl) of racemate (XLIX) (preferably the 4O-acetyl and 4-O-propionyl derivatives) with an appropriate microorganism, preferably a Saccharomyces species e.g., 1375-143, affords preferential de-O-acylation of the 4(R)-enantiomer to give (LI), which is then separated from the unreacted 4(S)-O-acyl enantiomer (LII) by chromatographic procedures. After separation, mild hydrolysis of the 4(S) derivative (LII) provides the 4(S)-hydroxycyclopentenone (LIII). [See N. J. Marsheck and M. Miyano, Biochima et Biophysica Acta, 316, 363 (1973) for related examples.]

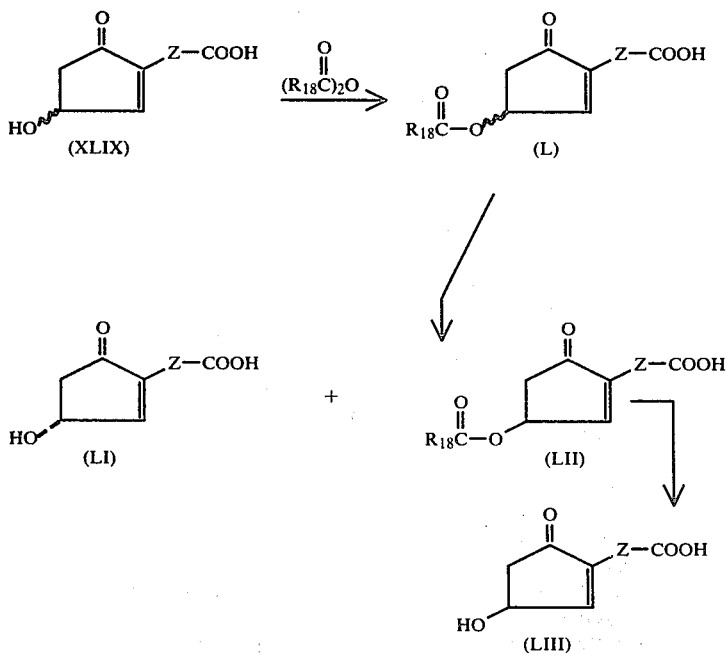

It is also possible to prepare the individual 4-hydroxycyclopentenones (LI) and (LIII) directly by selective microbial hydroxylations of the corresponding 4-unsubstituted cyclopentenone (LIV). For example, with *Aspergillus niger* ATCC 9142; a selective 4(R)-hydroxylation of [LIV, $Z=(CH_2)_6$] has been reported; see S. Kurozumi, T. Tora and S. Ishimoto, *Tetrahedron Letters*, 4959 (1973). Other microorganisms can also accomplish this hydroxylation.

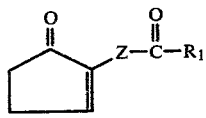
(LIV)

An alternative resolution procedure involves derivatization of the alcohol function of the racemic hydroxycyclopentenone to give ester-acid derivatives such as (LV) wherein $R_1''$ is hydrogen or an alkoxy group, n' is zero or two and z is as hereinabove defined.

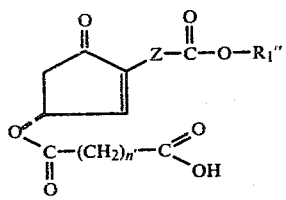
(LV)

Such derivatives may be obtained from the corresponding free hydroxycyclopentenone by treatment in the usual manner with oxalyl chloride, succinyl chloride, succinic anhydride and the like. Treatment of the resulting acid or diacid ($R_1''$=hydrogen) with optically active amines e.g., 1-(−)-α-methylbenzylamine, d-(+)-α-methylbenzylamine, brucine, dehydroabietylamine, strychnine, quinine, cinchonine, quinidine ephedrine, (+)-α-amino-1-butanol and the like, and fractional recrystallization of the resulting diastereomeric mixtures followed by cleavage of the 4-oxy ester function in each of the individually isolated diastereomers provides the individual 4(R)- and 4(S)-hydroxycyclopentenone enantiomers (LVI) and (LVII) or their respective esters. Cleavage of the oxalate acid ester (LV, n=O) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); For an example of the use of a succinate acid-ester see B. Goffinet, Ger. Offen. No. 2,263,880; *Chem. Abstracts*, 79, 7815z (1973).

Resolution of a 9-hydroxy racemate (the component enantiomers are illustrated by LVIII and LIX below) may be accomplished by conversion of the racemate, wherein the $C_{11}$ and $C_{15}$ or $C_{16}$ hydroxy functions have been preferentially blocked by trialkylsilyl groups, (for example, by first derivatizing the two hydroxy functions in the corresponding 9-oxo derivative and then reducing the 9-carbonyl as described hereinabove), to the corresponding phthalate half acid-ester, deblocking the $C_{11}$ and $C_{15}$ hydroxy functions and conversion of the diacid (e.g., LX) to a mixture of diastereomeric bis salts (e.g., LXI) with an optically active amine (e.g., 1-(−)-α-methylbenzylamine, D-(+)-α-methylbenzylamine, brucine, dehydroabietylamine, strychnine, quinine, cinchonine, cinchonidine, quinidine, ephedrine, deoxyephedrine, amphetamine, (+)-2-amino-1-butanol, (−)-2-amino-1-butanol and the like). The resulting diastereomers are then separated by fractional crystallization and the individual components are then converted by acidification and saponification to the individual optically active parent 9α-hydroxy enantiomers (LVIII) and (LIX), oxidation of which, after preferential blocking of the $C_{11}$ and $C_{15}$ hydroxy functions with tetrahydropyranyl or trialkylsilyl groups, provides, after deblocking, the corresponding individual 9-oxo-enantiomers (LXII) and (LXIII). If necessary, the 11- and 15-hydroxy groups can be converted to tetrahydropyranyloxy groups prior to saponification of the phthalate ester. (For an appropriate literature procedure see E. W. Yankee, C. H. Lin and J. Fried, *Journ. Chem. Soc.*, 1972, 1120).

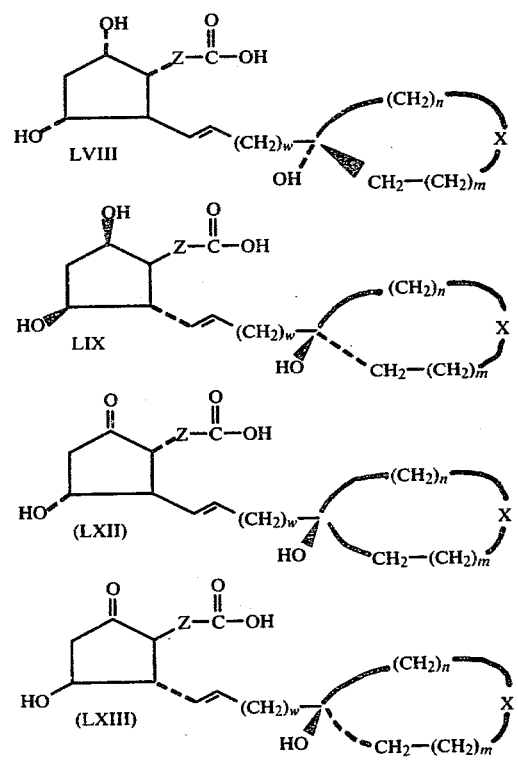

Another procedure involves conversion of the 9α-hydroxy racemate (as the prostenoic acid ester and with the $C_{11}$ and $C_{15}$ alcohol functions preferentially blocked as trialkylsilyl ethers) to the diastereomeric carbamates with an optically active isocyanate, e.g., (+)-1-phenylethylisocyanate or (−)-1-phenylethylisocyanate, followed by deblocking. Separation of the resulting diastereomers, for example (LXIV) and (LXV), can be accomplished by fractional cyrstallization or by the usual chromatographic procedures, or if necessary by high speed liquid chromatography involving, recycling techniques. Base-treatment of the individual diastereomeric carbamates affords the individual diastereomeric alcohols, for example (LVIII) and (LXVI).

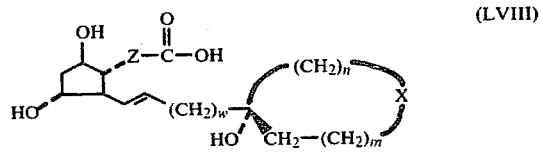
(LVIII)

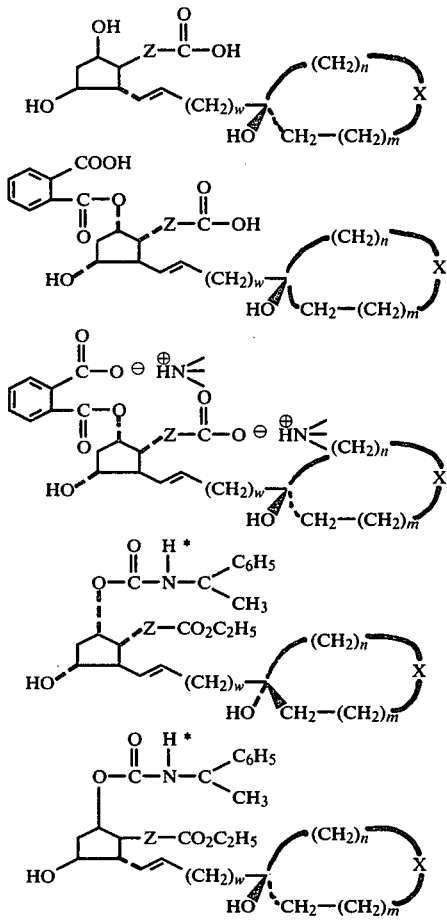

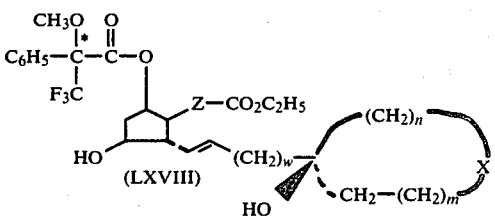

It is also possible to effect resolution of the 9α-hydroxy racemate, preferably as the prostenoate ester, by esterification of the 9α-hydroxy function (prior preferential blocking as discussed hereinabove of $C_{11}$ and $C_{15}$ or $C_{16}$ hydroxy functions as tetrahydropyranyl or trialkylsilyl ethers) with an optically active acid, via its acid chloride followed by deblocking the $C_{11}$ and $C_{15\,or}$ $C_{16}$ alcohol groups. Suitable optically active acids include -camphoric acid, menthoxyacetic acid, 3α-acetoxy-$\Delta^5$-etianic acid, $(-)$-α-methoxy-α-α-trifluoromethylphenylacetic acid and $(+)$-α-methoxy-α-trifluoromethylphenylacetic acid, and the like. The resulting diastereomeric esters, for example, (LXVII) and (LXVIII), are then separated by fractional crystallization or by chromatographic techniques including, if necessary, the use of high speed liquid chromatography. Saponification of the individual diastereomers then provides the individual 9α-hydroxy-rostenoic acid enantiomers (LVIII) and (LXVI).

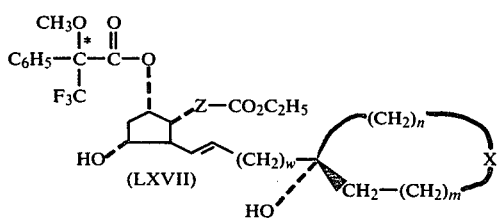

Dehydration as described above, of the optically active PGE compounds then furnishes the PGA compounds in their optically active forms. Treatment of the optically active PGE compounds with base as described above, furnishes the corresponding optically active PGB compounds. The optically active 11-cyano derivatives are formed by the reaction of the optically active PGA compounds with acetone cyanohydrin as described above.

The preparation of the requisite cyclopentenones which contain a sulfur atom in the α-chain is described in Flowsheet C. In accordance with Flowsheet C wherein t is hereinabove described, treatment of 2-furyllithium (LXXIII) with a ω-chloroaldehyde (LXXIV) provides the chlorolcohol (LXXV). Treatment of the chloroalcohol (LXXV) with ethylmercaptoacetate furnishes the hydroxy ester (LXXVI) which upon hydrolysis with sodium formate/formic acid provides the 3-hydroxy-cyclopentenone (LXXVII). Treatment of the cyclopentenone (LXXVII) with sulfuric acid provides the required 4-hydroxy-cyclopentenone (LXXVIII) which after treatment with chlorotrimethylsilane and hexamethyl disilazene in pyridine provides the bissilylated cyclopentenone (LXXIX).

The 3-hydroxy-cyclopentenones of the type (LXXVII), the 4-hydroxy-cyclopentenones of the type (LXXXVIII), and the bissilylated or bistetrahydropyrayl protected or other suitably protected 4-hydroxy-cyclopentenone of the type (LXXIX) are novel and useful compounds which are also embraced by this invention, as are the novel intermediates required for their preparation.

Flowsheet C

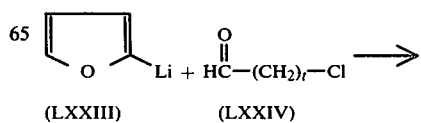

-continued
Flowsheet C

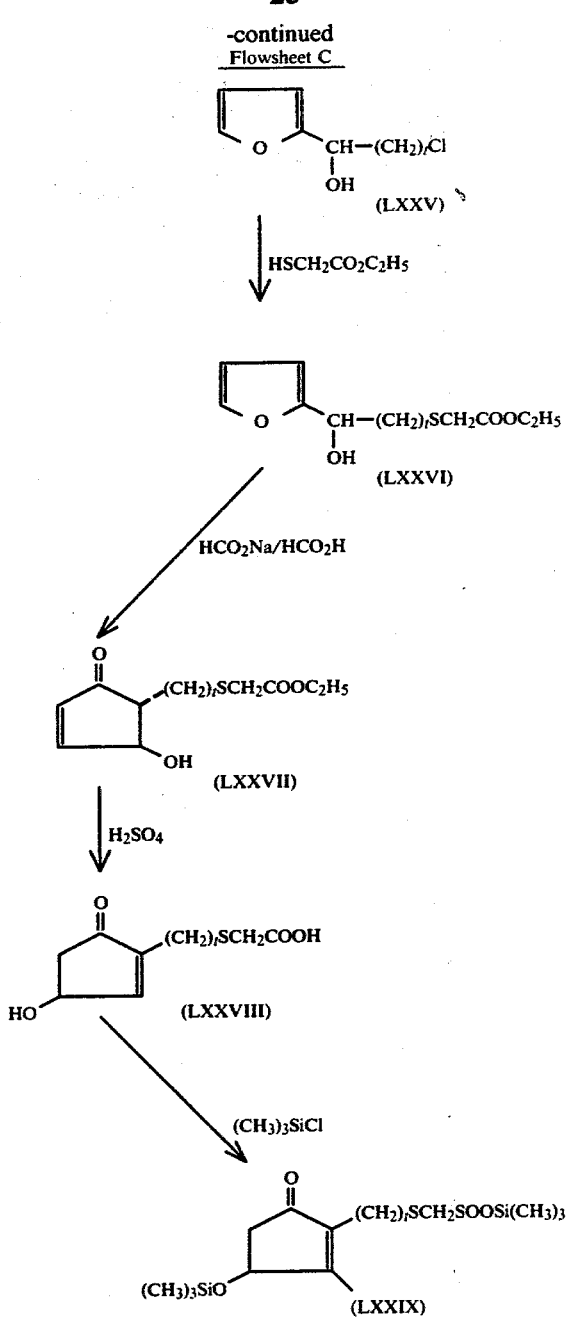

The ring system of certain of the novel compounds of this invention allow them to be characterized as follows:

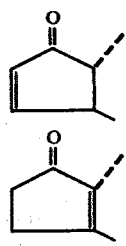

PGA-Type

PGB-Type

The novel compounds of this invention possess the pharmacological activity described below as associated with the appropriate above-described prostaglandin type.

The known PGA and PGB compounds are all potent in causing multiple biological responses even at low doses. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity then the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively, orally, sublingually, intravaginally, bucally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGA and PGB compounds, and their esters and pharmacologically acceptable salts, are extremely potent in causing various biological responses. For that reason, these compounds are useful for pharmacological purposes. See, for example, Bergstrom, et al., Pharmacol. Rev., 20, 1 (1968), and references cited therein. A few of those biological responses are systemic arterial blood pressure lowering in the case of the PGA compounds as measured, for example, in anesthetized (phenobarbital sodium) pentolinium-treated rats with indwelling aortic and right heart cannulas; stimulation of smooth muscle as shown, for example by tests on strips of guinea pig ileum, rabbit duodenum, or gerbil colon; potentiation of other smooth muscle stimulants; antilipolytic activity as shown by antagonism of epineephrine-induced mobilization of free fatty acids or inhibition of the spontaneous release of glycerol from isolated rat fat pads; inhibition of gastric secretion in the case of the PGA compounds as shown in dogs with secretion stimulated by food or histamine infusion; activity on the central nervous system; and in the case of PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

The PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg to about 500 μg per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGA compounds are useful as hypotensive agents to reduce blood pressure in mammals including man. For this purpose, the compounds are administered by intravenous infusion at the rate about 0.01 to about 50 μg per kg of body weight per minute, or in a single or multiple doses of about 25 to 2500 μg per kg. of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorena syndrome and early kidney transplant rejection. In case of excessive or inappropriate ADH (antidiuretic hormone vasopressin) secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably adminstered topically at or near the site where call growth and keratin formation is desired, advantageously as an aerosol liquid or micronized powder spray, as an isotonic aqueous solution in the case of wet dressing, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing one to 500 μg/ml of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example hydrocortisone, prednisolone, methylprednisolone, and fluprednisolone, each of those being used in the combination at the usual concentration suitable for its use alone.

The novel compounds of this invention induce the biological responses described hereinabove as associated with its particular prostaglandin type. These novel compounds are accordingly useful for the above-described corresponding purposes in the same manner as described above.

The novel PGA compounds of this invention are also useful as bronchodilators for the treatment of asthma and chronic bronchitis; as such they may be conveniently administered by inhalation of aerosol sprays prepared in a dose range of about 10 μg to about 10 mg. per ml. of a pharmacologically suitable liquid vehicle.

These derivatives described hereinabove are also more selective in their biological action and induce a more prolonged effect than the corresponding natural prostaglandins. These preparations are novel, completely unanticipated and provide distinct and important advantages.

In addition, certain of the novel compounds of this invention are useful for the preparation of other novel compounds of this invention.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The compounds of the present invention exhibit the ability to inhibit platelet aggregation in vitro when tested by the following procedure.

Human protein rich plasma is incubated with modified Tyrode's solution in a proportion of 40-50% human protein rich plasma. The test compounds are added at varying concentrations and after 5 minutes incubation, an aggregating agent such as adenosine diphosphate or collagen is added. The change in optical density (light transmission) is monitored by eye and inhibition is recorded as a (−) or lack of inhibition is recorded as a (+). Test compounds are considered active if they inhibit adenosine diphosphate or collagen induced aggregation at a concentration of 25 mcg/ml or less within 5-10 minutes. The results of this test on representative compounds of this invention appear in Table A.

TABLE A

| | Inhibition of Platelet Aggregation - In Vitro | | | | | | | |
|---|---|---|---|---|---|---|---|---|
| | Adenosine Diphosphate Drug Concentration μg/ml | | | | Collagen Drug Concentration μg/ml | | | |
| Compound | 250 | 25 | 2.5 | 0.25 | 250 | 25 | 2.5 | 0.25 |
| nat(and ent)-15-Hydroxy-9-oxo-15,16-tetramethylene-17,18,19,20-tetranor-13-trans,5-cis,10-prostatrienoic acid | (−) | (+) | | | (−) | (+) | | |
| nat(and ent)-9α/β-Cyano,15-hydroxy-9-oxo-15,16-tetramethylene-17,18,19,20-tetranor-5-cis-13-trans-prostadienoic acid | (−) | (−) | (−) | | (−) | (−) | | |

(−) = Inhibition
(+) = No inhibition

The compounds of this invention are also useful as bronchodilators and accordingly have potential application in the treatment of asthma.

Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, Arzeneimittel-Forschung, 18, 995 (1968).] In Table B bronchodilator activity for representative compounds of this invention against one or more of the three spasmogenic agents is expressed as an $ED_{50}$ determined from the results obtained with three logarithmic cumulative intravenous doses.

TABLE B

| | Bronchodilator Activity | | |
|---|---|---|---|
| | $ED_{50}$, mg/kg | | |
| Compound | 5-Hydroxytryptamine | Histamine | Acetylcholine |
| nat(and ent)-9α/β-Cyano,15-hydroxy-9-oxo-15,16-tetramethylene-17,18,19,20-tetranor-5-cis-13-trans-prostadienoic acid | $1.81 \times 10^{-3}$ | $367 \times 10^{-6}$ | $2.74 \times 10^{-3}$ |
| nat(and ent)-15-Hydroxy-9-oxo-15,16-tetramethylene-17,18,19,20-tetranor-13-trans,5-cis,10-prostatrienoic acid | $>3.2 \times 10^{-3}$ | $632 \times 10^{-6}$ | $>3.2 \times 10^{-3}$ |

The invention will be described in greater detail in conjunction with the following specific examples.

EXAMPLE 1

Preparation of trans-1-Hydroxy-2-(3-trifluoromethyl)phenoxycyclopentane

A mixture of 88 g of cyclopentene oxide, 150.7 g of 3-trifluoromethylphenol, 5.0 g of sodium hydroxide in 30 ml of water and 4.0 g of methyltricaprylyl ammonium chloride is stirred at 70°-80° C. for 51 hours and at 25° C. for 96 hours. The mixture is then diluted with methylene chloride and poured into water. The organic layer is washed with dilute sodium hydroxide solution and water. The solution is dried over magnesium sulfate. The solvent is removed giving 221.5 g of a liquid which is distilled (bp 110°-113° C. 0.8 mm) giving trans-1-hydroxy-2-(3-trifluoromethyl)phenoxycyclopentane.

EXAMPLE 2

In the manner described above in Example 1 from 4-fluorophenol and cyclopentane epoxide is prepared trans-1-hydroxy-2-(4-fluoro)phenoxycyclopentane.

EXAMPLE 3

In the manner described above in Example 1 from 3-chlorophenol and cyclopentane epoxide is prepared trans-1-hydroxy-2-(3-chloro)phenoxycyclopentane.

EXAMPLE 4

Preparation of 2-(3-Trifluoromethylphenoxy)cyclopentanone

To a suspension of 327.43 g of pyridinium chlorochromate in one liter of methylene chloride is added 220 g of trans-1-hydroxy-2-(3-trifluoromethylphenoxy)cyclopentane in 500 ml of methylene chloride. The mixture is stirred for 2 hours 15 minutes. Another 50 g of the oxidizing agent is added and the mixture is stirred for 4½ hours. The mixture is diluted with ether and decanted from a black residue which is washed with more ether. The combined solutions are filtered through silica gel. The solvent is removed. The residue is dissolved in ether and again filtered through silica-gel. The solvent is removed and the residue is distilled (bp 113°-116° C., 1.5 mm) to give 188 g of 2-(3-trifluoromethylphenoxy)cyclopentanone.

EXAMPLE 5

In the manner described above for Example 4 is prepared from the product of Example 2; 2-(4-fluorophenoxy)cyclopentanone.

EXAMPLE 6

In the manner described above for Example 4 is prepared from the product of Example 3; 2-(3-chlorophenoxy)cyclopentanone.

EXAMPLE 7

Preparation of 1R,2S(and 1S,2R)-1-Ethynyl-1-hydroxy-2-butylcyclopentane and 1R,2R(and 1S,2S)-1-ethynyl-1-hydroxy-2-butylcyclopentane Into 150 ml of dry tetrahydrofuran is bubbled purified acetylene, as a solution of 2.4M n-butyl magnesium chloride (92 ml) is added dropwise with stirring over a 2 hour period. To the resulting solution of acetylene magnesium chloride is added 21 g of 2-butylcyclopentanone in 50 ml of tetrahydrofuran dropwise over 15 minutes. The solution is stirred for 30 minutes and then is poured into an ice cold solution of saturated ammonium chloride. The mixture is acidified to pH 5 and extracted with ether. The ether solution is washed with brine and dried over magnesium chloride. The ether is removed and the residue is distilled giving 14.8 g of a colorless liquid. This is chromatographed on a dry column of silica-gel eluting with benzene-ethyl acetate (19:1) to separate isomers giving 1R,2S(and 1S,2R)-1-ethynyl-1-hydroxy-2-butylcyclopentane and 1R,2R(and 1S,2S)-1-ethynyl-1-hydroxy-2-butylcyclopentane.

EXAMPLE 8

Preparation of 1-propargyl-1-hydroxycyclohexane

A stirred suspension of 121.6 g (5.0 mol) of magnesium in 1-l of anhydrous ether is treated with 0.6 g of mercuric chloride and about 100 mg of iodine. After several minutes, 3 ml of propargyl bromide is added and if no exotherm is noted, a small amount of reacting propargyl bromide and magnesium in ether is added. When the reaction begins, a mixture of 5.0 mol of cyclohexanone and 595 g (5.0 mol) of propargyl bromide is added dropwise at a rate that produces vigorous refluxing of the solution. (The propargyl bromide must always be present in some excess otherwise the reaction will stop. If this happens, the addition of about 1 ml of propargyl bromide will restart the reaction.) After about half of the propargy bromide-cyclohexanone mixture has been added, another 500–750 ml of ether is used to dilute the reaction mixture. At the end of the addition, the reaction mixture is refluxed for at least 0.5 hour, cooled and poured into 4 liters of saturated ammonium chloride during good stirring. The ethereal layer is separated and the aqueous layer is washed with ether several times and the combined extract is washed twice with saturated sodium chloride solution and dried over anhydrous magnesium sulfate. Evaporation of the ether yields 583 g (630 g theory) of a dark oil which is distilled giving purified 1-propargyl-1-hydroxycyclohexane.

EXAMPLES 9–27

In the manner of Examples 7 and 8 described above the following acetylenic alcohols listed in Table I were prepared from the acetylenic Grignard reagent and ketone specified.

Table I

| Example | Grignard Reagent | Ketone | Acetylenic Alcohol |
| --- | --- | --- | --- |
| 9 | acetylene magnesium chloride | cyclohexanone | 1-ethynyl-1-hydroxycyclohexane |
| 10 | acetylene magnesium chloride | cyclopentanone | 1-ethynyl-1-hydroxycyclopentane |
| 11 | acetylene magnesium chloride | cycloheptanone | 1-ethynyl-1-hydroxycycloheptane |
| 12 | acetylene magnesium chloride | 3-propylcyclopentanone | 1R,3S-(and 1S,3R-) 1-ethynyl-1-hydroxy-3-propylcyclopentane |
| 13 | acetylene magnesium chloride | 3-propylcyclopentanone | 1R,3R-(and 1S,3S-) 1-ethynyl-1-hydroxy-3-propylcyclopentane |
| 14 | acetylene magnesium chloride | 2-butylcyclohexanone | 1R,2S-(and 1S,2R-) 1-ethynyl-1-hydroxy-2-butylcyclohexane |
| 15 | acetylene magnesium chloride | 2-butylcyclohexanone | 1R,2R-(and 1S,2S-) 1-ethynyl-1-hydroxy-2-butylcyclohexane |
| 16 | acetylene magnesium chloride | 2-(3-trifluoromethylphenoxy)-cyclopentanone | 1R,2S-(and 1S,2R-) 1-ethynyl-1-hydroxy-2-(3-trifluoromethylphenoxy)cyclopentane |
| 17 | acetylene magnesium chloride | 2-(3-trifluoromethylphenoxy)-cyclopentanone | 1R,2R-(and 1S,2S-) 1-ethynyl-1-hydroxy-2-(3-trifluoromethylphenoxy)cyclopentane |
| 18 | acetylene magnesium chloride | 2-(4-fluorophenoxy)cyclopentanone | 1R,2S-(and 1S,2R-) 1-ethynyl-1-hydroxy-2-(4-fluorophenoxy)cyclopentane |
| 19 | acetylene magnesium chloride | 2-(4-fluorophenoxy)cyclopentanone | 1R,2R-(and 1S,2S-) 1-ethynyl-1-hydroxy-2-(4-fluorophenoxy)cyclopentane |
| 20 | acetylene magnesium chloride | 2-(3-chlorophenoxy)-cyclopentanone | 1R,2S-(and 1S,2R-) 1-ethynyl-1-hydroxy-2-(3-chlorophenoxy)cyclopentane |
| 21 | acetylene magnesium chloride | 2-(3-chlorophenoxy)-cyclopentanone | 1R,2R-(and 1S,2S-) 1-ethynyl-1-hydroxy-2-(3-chlorophenoxy)cyclopentane |
| 22 | acetylene magnesium chloride | 3-methylcyclohexanone | 1R,3S-(and 1S,3R-) 1-ethynyl-1-hydroxy-3-methylcyclohexane |
| 23 | acetylene magnesium chloride | 3-methylcyclohexanone | 1R,3R-(and 1S,3S-) 1-ethynyl-1-hydroxy-3-methylcyclohexane |
| 24 | propargyl magnesium bromide | 2-butylcyclopentanone | 1R,2S-(and 1S,2R-) 1-propargyl-1-hydroxy-2-butylcyclopentane |
| 25 | propargyl magnesium bromide | 2-butylcyclopentanone | 1R,2R-(and 1S,2S-) 1-propargyl-1-hydroxy-2-butylcyclopentane |
| 26 | propargyl magnesium bromide | 2-(3-trifluoromethylphenoxy)-cyclopentanone | 1R,2S-(and 1S,2R-) 1-propargyl-1-hydroxy-2-(3-trifluoromethylphenoxy)cyclopentene |
| 27 | propargyl magnesium bromide | 2-(3-trifluoromethylphenoxy)-cyclopentanone | 1R,2R-(and 1S,2S)-1-propargyl-1-hydroxy-2-(3-trifluoromethylphenoxy)cyclopentanane |

EXAMPLE 28a

Preparation of 1R,2S(and 1S,2R)-1-Ethynyl-1-trimethylsilyloxy-2-butylcyclopentane To a solution of 29.4 g of 1R,2S(and 1S,2R)-1-ethynyl-1-hydroxy-2-butylcyclopentane and 30.2 g of imidazole in 180 ml of dimethylformamide is added at 0° C. with stirring 24.1 g of trimethylsilylchloride. The mixture is stirred for 3 hours. The mixture is poured into 700 ml of hexane and washed twice with water and once with brine. The ether solution is dried over magnesium sulfate. The solvent is removed and the residue is distilled (bp 64°–72° C., 0.6 mm) to give 35.8 g of 1R,2S(and 1S,2R)-1-ethynyl-1-trimethylsilyloxy-2-butylcyclopentane.

EXAMPLE 28b

Preparation of 1R,2R(and 1S,2S)-1-Ethynyl-1-trimethylsilyloxy-2-butylcyclopentane To a mixture of 45.0 g of 1R,2R(and 1S,2S)-1-ethynyl-1-hydroxy-2-butylcyclopentane and 46.2 g of imidazole in 255 ml of dimethylformamide at 0° C. under nitrogen is added 36.9 g of trimethylsilylchloride. The mixture is stirred at room temperature for 3 hours and then poured into 700 ml of hexane. Water is added, the organic layer is separated and the water layer is extracted with hexane. The combined hexane solutions are washed twice with water and dried over magnesium sulfate. The solvent is removed and the residue is distilled giving the product as 53 g of a colorless oil.

EXAMPLE 28c

Preparation of 1-Ethynyl-1-trimethylsilyloxycyclohexane

A 194 g portion of imidazole and 158.2 g of 1-ethynylcyclohexan-1-ol are mixed with 500 g of dimethylformamide with cooling in an ice bath. A 152 g portion of trimethylchlorosilane is added with cooling and stirring in about one minute. The mixture is stirred for one hour and allowed to stand overnight. One liter of hexane is added. The lower layer is separated, diluted with water and extracted with hexane. The hexane layers are washed several times with water and then combined and dried over magnesium sulfate. Filtration and then evaporation of the hexane gives 198.5 g of product which is distilled giving 168 g of the desired product.

EXAMPLE 28d

Preparation of 1-Propargyl-1-trimethylsilyloxycyclohexane

To a stirred solution of 55.4 g of 1-(2-propyn-1--yl)cyclohexanol [H. Gutmann, et al., *Helv. Chim. Acta*, 42, 719 (1959)] and 79 g of imidazole in 240 ml of DMF at 10° C. initially is added 56 ml of chlorodimethylsilane during 10 minutes. The cloudy yellow solution is stirred at room temperature for 26 hours. The resulting mixture is partitioned between 1000 ml of hexane and 400 ml of water at 0°-5° C. The hexane phase is washed successively with 6×200 ml of cold water and 200 ml of brine. The extract is dried over magnesium sulfate, filtered, and evaporated to give 85 g of colorless liquid, i.r. (film):1240 and 830 cm$^{-1}$ (trimethylsilyloxy group).

EXAMPLE 29a

Preparation of 1R,2S(and 1S, 2R)-1-(trans-2-Iodovinyl)-1-trimethylsilyloxy-2-butylcyclopentane To a mixture of 9.2 g of sodium borohydride and 45.8 g of 2-methyl-2-butene in 350 ml of dry tetrahydrofuran at 0° C. with stirring under nitrogen is added, over 20 minutes, 41.1 ml of boron trifluoride etherate. After 3 hours, to this resulting solution of diisoamylborane is added 38.8 g of 1R, 2S (and 1S, 2R)-1-ethynyl-1-trimethylsilyloxy-2-butylcyclopentane in 40 ml of tetrahydrofuran in 20 minutes. The mixture is stirred 2 hours and then stored at −20° C. overnight. The mixture is allowed to warm to 0° C. and at 0° C. 85 g of dry trimethylamineoxide is added portionwise over 20 minutes. After stirring at 25° C. for one hour, the mixture is filtered through diatomaceous earth. The filtrate is poured simultaneously with a solution of 230 g of iodine in 250 ml of tetrahydrofuran into a stirred, cold solution of 430 g of sodium hydroxide in 1900 ml of water. After stirring for 30 minutes, the organic layer is separated. The aqueous layer is extracted with ether. The combined organic solutions are washed twice with a saturated solution of sodium thiosulfate and once with brine. The solution is dried over magnesium sulfate, the solvent is removed and the residue is dissolved in hexane. The hexane solution is filtered through diatomaceous earth and silica gel. The hexane is removed and the residue is purified by dry column chromatography on silica gel eluting with hexane: 45.35 g of 1R,2S(and 1S,2R)-1-(trans-2-iodovinyl)-1-trimethylsilyloxy-2-butylcyclopentane is obtained.

EXAMPLE 29b

Preparation of 1R,2R(and 1S,2S)-1-(trans-2-Iodovinyl)-1-trimethylsilyloxy-2-butylcyclopentane To a mixture of 12.22 g of sodium borohydride and 60.82 g of 2-methyl-2-butene in 450 ml of tetrahydrofuran under nitrogen at 0° C., is added 54.6 ml of boron trifluoride etherate, dropwise over a 20 minute period. The solution is stirred at 0° C. for 2 hours and then at room temperature for 30 minutes. This solution is cooled to 0° C. and 55.5 g of 1R,2R(and 1S,2S)-1-ethynyl-1-trimethylsilyloxy-2-butylcyclopentane in 50 ml of tetrahydrofuran is added. The mixture is allowed to stand in a cold room overnight. To this mixture at 0° C. is added with stirring 112.8 g of trimethylamine oxide over a 20 minute period. The mixture is stirred at room temperature for 90 minutes and then filtered. To the filtrate is added simultaneously a solution of 565 g of sodium hydroxide in 2000 ml of water and a solution of 300 g of iodine in 300 ml of tetrahydrofuran. The mixture is stirred 30 minutes, the organic layer is separated and the aqueous layer is extracted with ether. The combined organic solutions are washed with saturated sodium thiosulfate solution and with saturated sodium chloride solution. The solution is dried with magnesium sulfate and filtered through a pad of silica gel. The solution is removed giving an orange liquid which is chromatographed on a dry column of silica gel giving 59.5 g of the product as a yellow liquid.

EXAMPLE 30

Preparation of 2-(3-Tri-n-butylstannyl-2-trans-propenyl)-1-trimethylsilyloxycyclohexane To a stirred mixture of 31/5 g of 1-propargyl-1-trimethylsilyloxycyclohexane and 150 mg of azobisisobutyronitrile is added 41 ml of tri-n-butyltin hydride. The stirred mixture is heated to about 80° C. The initial exothermic reaction is moderated, and the temperature is subsequently maintained at 130°-135° C. for one hour.

The product is distilled to afford 56 g of colorless liquid, bp 150°-160° C. (0.15-0.3 mm), pmr (CDCl$_3$): 6.0 (multiplet, vinyl protons).

EXAMPLES 31–50

Using the procedure outlined above for Examples 28a, b, c and d, the acetylenic alcohols listed in Table II are converted to their corresponding acetylenic trimethylsilyloxy derivatives; these in turn using the procedure outlined above for Examples 29a and 29b, were converted to their corresponding trans-2-iodovinyl derivatives or using the procedure out above for Example 30, were converted to their corresponding trans-2-tri-n-butylstannyl derivatives (Table II).

Table II

| Example | Acetylene of Example | Method of Example | Vinyl Iodide or Vinyl Tin Compound |
|---------|---------------------|-------------------|-------------------------------------|
| 31 | 9 | 29 | 1-(trans-2-iodovinyl)-1-trimethylsilyloxy-cyclohexane |
| 32 | 10 | 29 | 1-(trans-2-iodovinyl)-1-trimethylsilyloxy-cyclopentane |
| 33 | 11 | 30 | 1-(trans-2-tri-n-butylstannylvinyl)-1-trimethylsilyloxycycloheptane |
| 34 | 12 | 29 | 1R,3S-(and 1S,3R-) 1-(trans-2-iodovinyl)-1-trimethylsilyloxy-3-propylcyclopentane |
| 35 | 13 | 29 | 1R,3R-(and 1S,3S-) 1-(trans-2-iodovinyl)-1-trimethylsilyloxy-3-propylcyclopentane |
| 36 | 7 | 29 | 1R,2R-(and 1S,2S-) 1-(trans-2-iodovinyl)-1-trimethylsilyloxy-2-butylcyclopentane |
| 37 | 14 | 29 | 1R,2S-(and 1S,2R-) 1-(trans-2-iodovinyl)-1-trimethylsilyloxy-2-butylcyclohexane |
| 38 | 15 | 29 | 1R,2R-(and 1S,2S-) 1-(trans-2-iodovinyl)-1-trimethylsilyloxy-2-butylcyclohexane |
| 39 | 16 | 30 | 1R,2S-(and 1S,2R-) 1-(trans-2-tri-n-butylstannylvinyl)-1-trimethylsilyloxy)-2-(3-trifluoromethylphenoxy)cyclopentane |
| 40 | 17 | 30 | 1R,2R-(and 1S,2S-) 1-(trans-2-tri-n-butylstannylvinyl)-1-trimethylsilyloxy-2-(3-trifluoromethylphenoxy)cyclopentane |
| 41 | 18 | 29 | 1R,2S-(and 1S,2R-) 1-(trans-2-iodovinyl)-1-trimethylsilyloxy-2-(4-fluorophenoxy)-cyclopentane |
| 42 | 19 | 29 | !R,2R-(and 1S,2S-) 1-(trans-2-iodovinyl)-1-trimethylsilyloxy-2-(4-fluorophenoxy)-cyclopentane |
| 43 | 20 | 30 | 1R,2S-(and 1S,2R-) 1-(trans-2-tri-n-butylstannylvinyl)-1-trimethylsilyloxy-2-(3-chlorophenoxy)cyclopentane |
| 44 | 21 | 30 | 1R,2R-(and 1S,2S-) 1-(trans-2-tri-n-butylstannylvinyl)-1-trimethylsilyloxy-2-(3-chlorophenoxy)cyclopentane |
| 45 | 22 | 29 | 1R,3S-(and 1S,3R-) 1-(trans-2-iodovinyl)-1-trimethylsilyloxy-3-methylcyclohexane |
| 46 | 23 | 29 | 1R,3R-(and 1S,3S-) 1-(trans-2-iodovinyl)-1-trimethylsilyloxy-3-methylcyclohexane |
| 47 | 24 | 30 | 1R,2S-(and 1S,2R-) 1-(3-tri-n-butylstannyl-2-trans-propenyl)-1-trimethylsilyloxy-2-butylcyclopentane |
| 48 | 25 | 30 | 1R,2R-(and 1S,2S-) 1-(3-tri-n-butylstannyl-2-trans-propenyl)-1-trimethylsilyloxy-2-butylcyclopentane |
| 49 | 26 | 30 | 1R,2S-(and 1S,2R-) 1-(3-tri-n-butylstannyl-2-trans-propenyl)-1-trimethylsilyloxy-2-(3-trifluoromethylphenoxy)cyclopentane |
| 50 | 27 | 30 | 1R,2R-(and 1S,2S-) 1-(3-tri-n-butylstannyl-2-trans-propenyl)-1-trimethylsilyloxy-2-(3-trifluoromethylphenoxy)cyclopentane |

EXAMPLE 51

Preparation of 2-(6-Carbotrimethylsilyloxyhex-2-cis-enyl)-4-trimethylsilyloxycyclopent-2-en-1-one To a solution of one g of 2-(6-carboxyhex-2-cis-enyl)-4-hydroxycyclopent-2-en-1-one in 12.5 ml of dry pyridine at 15° C. under argon is added with stirring 3.3 ml of hexamethyldisilazane (HMDS) followed by dropwise addition of 1.6 ml of trimethylchlorosilane (TMCS). The resulting mixture is stirred at ambient temperature for one hour then taken to dryness (vac. pump). The residue is taken up in hexanes and filtered thru Celite. Evaporation of the mother liquor followed by two evaporations with toluene furnished 1.5 g (96%) of pure 2-(6-carbotrimethylsilyloxyhex-2-cis-enyl)-4-trimethylsilyloxycyclopent-2-en-1-one.

EXAMPLE 52

Preparation of 2-(6-Carbotrimethylsilyloxyhexyl)-4-trimethylsilyloxycyclopent-2-en-1-one To a solution of one g of 2-(6-carboxyhexyl)-4-hydroxycyclopent-2-en-1-one in 12.5 ml of dry pyridine at 15° C. under argon, is added with stirring 3.3 ml of hexamethyl disilazane followed by dropwise addition of 1.6 ml of trimethylchlorosilane. The resulting mixture is stirred at ambient temperature for one hour and then taken to dryness. The residue is taken up in hexane and filtered through diatomaceous earth. Evaporation of the mother liquor followed by two evaporations with toluene gives pure product.

EXAMPLE 53

Preparation of 2-(6-carbomethoxyhexyl)-4(R)-trimethylsilyoxycyclopent-2-en-1-one To a solution of 1.0 g of 2-(6-carbomethylhexyl)-4(R)-hydroxycyclopent-2-en-1-one [R. Pappo, et al., Tetrahedron Letters, 943 (1973)] in 12.5 ml of dry pyridine at 15° under argon was added with stirring 3.3 ml (24 moles) of hexamethyldisilazone (HMDS) followed by dropwise addition of 1.6 ml (20.5 moles) of trimethylchlorosilane (TMCS). The resulting mixture was stirred at ambient temperature for 1 hour then taken to dryness (vac. pump). The residue is taken up in hexanes and filtered thru Celite. Evaporation of the mother liquid followed by two evaporations with toluene furnished pure 2-(6-carbomethoxyhexyl)-4(R)-trimethylsilyloxyhexyl)-4(R)-trimethylsilyloxycyclopent-2-en-1-one.

EXAMPLE 54

Preparation of 2-(6-carbomethoxyhexyl)-4(S)-trimethylsilyloxycyclopent-2-en-1-one In the manner described in Example 53 treatment of 2-(6-carbomethoxyhexyl)-4(S)-hydroxycyclopent-2-en-1-one [R.Pappo, et al., Tetrahedron Letters, 943 (1973)] with hexamethyldisilazane and trimethylsilylchloride gives the subject product.

EXAMPLE 55

Preparation of 5-chloro-1-(2-furyl)-1-pentanol

To a stirred suspension of 2-furyllithium (prepared from 0.53 moles of n-butyllithium and 39.5 g of furan by the procedure of *J. Org. Chem.*, 27, 1216 (1962) in 350 ml of ether and ca. 200 ml of hexane at $-78°$ is added a solution of 57.9 g of 5-chloropentanol (*Chem. Abstr.*, 59. 7579F (1963)) in 80 ml of ether during 25 minutes. The mixture is warmed to 0° during 20 minutes, stirred at 0° for 15 minutes, and treated with 140 ml of saturated ammonium chloride. The ether phase is washed with water and brine, dried over magnesium sulfate and potassium carbonate mixture, and concentrated to give a liquid, pmr spectrum (CDCl$_3$): $\delta$ 3.59 (triplet, C$\underline{H}_2$Cl$_2$) and 4.70 (triplet, CH$_2$C$\underline{H}$OH).

EXAMPLE 56

Preparation of 5-(carbethoxymethylthio)-1-(2-furyl)-1-pentanol

To a stirred, refluxing mixture of 76 g of ethyl mercaptoacetate, 79.5 g of 5-chloro-1-(2-furyl)-1-pentanol and 10 ml of 1.5M sodium ethoxide in ethanol is added an additional 300 ml of 1.5m sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): $\delta$ 3.24 (singlet, —S—CH$_2$CO$_2$C$_2$H$_5$) and 4.70 (triplet, CH$_2$CHOH).

EXAMPLE 57

Preparation of 2-(6-carboxy-5-thiahexyl)-4-hydroxycyclopent-2-en-1-one

A stirred solution of 125 g of 5-(carbethoxymethylthio)-1-(2-furyl)-1-pentanol, 22.4 g of sodium formate, 250 ml of dioxane and 1330 ml of water is refluxed for 20 hours.

The solution, containing crude 3-hydroxy-2-[4-(carbethoxymethylthio)butyl]cyclopent-4-en-1-one, is cooled and treated during 10 minutes with 75 ml. of sulfuric acid (d=1.84) with stirring. The stirred solution is refluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil, pmr spectrum (CDCl$_3$): $\delta$3.24 (singlet, —S—CH$_2$—CO$_2$C$_2$H$_5$), 5.0 (broad singlet —CHOH—).

EXAMPLE 58

Preparation of 2-(6-carbotrimethylsilyloxy-5-thiahexyl)-4-trimethylsiloxycyclopent-2-en-1-one To a stirred solution of 28.4 g of 4-hydroxy-2-[4-(carboxymethylthio)butyl9 cyclopent-2-3n-1-one and 76 ml of hexamethyldisilazane in 330 ml of pyridine at 5° C. is added 38 ml of chlorotrimethylsilane during 5 minutes. The mixture is stirred at ambient temperature for 3.5 hours, at 45° C. for 5 minutes, and then evaporated to remove solvent. The residue is stirred with 1000 ml of petroleum ether and filtered. The filtrate is treated with charcoal and filtered; this filtrate is concentrated with the aid of toluene to give a liquid, pmr spectrum (CDCl$_3$): 0.18 (singlet, trimethylsiloxy group) and 0.28 (singlet, trimethylsiloxycarbonyl group).

EXAMPLE 59

Preparation of 4-chloro-1-(2-furyl)-1-butanol

To a stirred suspension of 2-furyllithium [prepared from 0.53 moles of n-butyllithium and 39.5 g of furan by the procedure of *J. Org. Chem.* 27, 1216 (1962)] in 350 ml. of ether and ca. 200 ml of hexane at $-78°$ C. is added a solution of 57.9 g of 4-chlorobutanol [*Chem. Abstr.*, 59, 7579F (1963)] in 80 ml of ether during 25 minutes. The mixture is warmed to 0° C. during 20 minutes, stirred at 0° C. for 15 minutes, and treated with 140 ml of saturated ammonium chloride. The ether phase is washed with water and brine, dried over magnesium sulfate and potassium carbonate mixture, and concentrated to give a liquid, pmr spectrum (CDCl$_3$): 3.59 (triplet, CH$_2$Cl) and 4.70 (triplet, CH$_2$CHOH).

EXAMPLE 60

Preparation of 4-carbethoxymethylthio)-1-(2-furyl)-1-butanol

To a stirred, refluxing mixture of 76 g of ethyl mercaptoacetate, 79.5 g of 4-chloro-1-(2-furyl)-1-butanol, and 10 ml of 1.5M sodium ethoxide in ethanol is added an additional 300 ml of 1.5M sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): 3.24 (singlet, —S—CH$_2$—CO$_2$C$_2$H$_5$) and 4.70 (triplet, CH$_2$CHOH).

EXAMPLE 61

Preparation of 2-(5-carboxy-4-thiapentyl)-4-hydroxycyclopent-2-en-1-one

A stirred solution of 125 g of 4-(carbethoxymethylthio)-1-(2-furyl)-1-butanol, 22.4 g of sodium formate, 250 ml of formic acid, and 400 mg of hydroquinone in 2000 ml of dioxane and 1330 ml of water is refluxed for 20 hours.

The solution, containing crude 3-hydroxy-2[3-(carbethoxymethylthio)propyl]cyclopent-4-en-1-one, is cooled and treated during 10 minutes with 75 ml of sulfuric acid (d=1.84) with stirring. The stirred solution is refluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil.

EXAMPLE 62

Preparation of 2-(5-carbotrimethylsilyloxy-4-thiapentyl)-4-trimethylsiloxycyclopent-2-en-1-one To a stirred solution of 28.4 g of 4-hydroxy-2-[4-(carboxymethylthio)butyl cyclopent-2-en-1-one and 76 ml. of hexamethyldisilazane in 330 ml of pyridine at 5° C. is added 38 ml of chlorotrimethylsilane during 5 minutes. The mixture is stirred at ambient temperature for 3.5 hours, at 45° C. for 5 minutes, and then evaporated to remove solvent. The residue is slurried with 1000 ml of petroleum ether and filtered. The filtrate is treated with charcoal and filtered; this filtrate is concentrated with the aid of toluene to give a liquid, pmr spectrum ($CDCl_3$): 0.18 (singlet, trimethylsiloxy group) and 0.28 (singlet, trimethylsiloxycarbonyl group).

EXAMPLE 65

Preparation of nat(and ent)-11,15-dihydroxy-9-oxo-15,16-tetramethylene-17,18,19,20-tetranor prostanoic acid A solution of nat(and ent(-11,15-dihydroxy-9-oxo-15,16-tetramethylene-17,18,19,20-tetranor-13-trans-prostanoic acid (800 mg) in 50 ml of ethyl acetate is hydrogenated in a Parr apparatus using 500 mg of 5% rhodium-on-carbon. The catalyst is removed by filtration and the filtrate is taken to dryness to furnish the titled product.

EXAMPLES 66–68

Hydrogenation of the prostenoic acids listed in Table II below in ethyl acetate using a rhodium-on-carbon catalyst in accordance with the method described in Example 65 gives the prostanoic acids of the table.

Table III

| Example | 13-trans-prostenoic acid of Example | Prostanoic Acid |
| --- | --- | --- |
| 66 | 74 | nat-15S,16R-(and ent-15R,16S)-11α,15-dihydroxy-9-oxo-15,16-trimethylene prostanoic acid |
| 67 | 75 | nat-15S,16R-(and ent-15R,16R)-11α,15-dihydroxy-9-oxo-15,16-trimethylene protanoic acid |
| 68 | 76 | nat-(and ent)-11α,16-dihydroxy-9-oxo-16,17-tetramethylene-18,19,20-trinor prostanoic acid |

EXAMPLE 69

Preparation of nat(and ent)-11α,15-Dihydroxy-9-oxo-15,16-tetramethylene-17,18,19,20-tetranor-5-cis,13-trans-prostadienoic Acid A 6.48 ml solution of 2.3M n-butyllithium in hexane is added, at 0° C. under nitrogen, to a solution of 1.64 g of thiophenol in 45 ml of ether. After one hour at 0° C. a solution of 5.85 g of tri-n-butylphosphine-copper complex in 140 ml of ether is added and the mixture is stored in a freezer overnight. To a solution of 4.54 g of 1-(trans-2-iodovinyl)-1-trimethylsilyloxycyclohexane in 8 ml of toluene at −40° C. under nitrogen is added, with stirring, 35 ml of a solution of t-butyllithium. After 90 minutes a few ml of ether is added and the mixture is stirred at room temperature for 15 minutes. This solution is recooled to −78° C. and the copper solution is cooled to 31 78° C. and transferred to the vinyl lithium solution in a steady stream. The solution is stirred at −78° C. for 35 minutes and a solution of 5.0 g of 2-(6-carbotrimethylsilyloxyhex-2-cis-enyl)-4-trimethylsilyloxycyclopent-2-en-1-one (Ex. 51) in 10 ml of ether is added. The mixture is placed in a bath at −45° C., stirred for 3 hours and allowed to warm to −20° C. over 15 minutes. A solution of 2.0 g of acetic acid in 5 ml of ether is added after recooling to −40° C. Saturated $NH_4Cl$ solution is added followed by a small amount of dilute HCl. The mixture is poured into ether. The aqueous layer is extracted with ether. The combined ether solutions are washed with dilute HCl, twice with water and then with saturated NaCl. The ether is dried over $MgSO_4$ and the solvent is removed giving a yellow oil. This is stirred in 50 ml of acetic acid:tetrahydrofuran:water (4:2:1) for 45 minutes and poured into water. The solution is extracted with ether and the ether solution is washed with water twice and once with brine. The solution is dried over magnesium sulfate and the solvent is removed. The residue is chromatographed on a dry column of silica gel eluting with ethyl acetate containing 1% acetic acid to give 2.15 g of nat(and ent)-11α,15-dihydroxy-9-oxo-15,16-tetramethylene-17,18,19,20-tetranor-5-cis,13-trans-prostadienoic acid.

EXAMPLE 70

Preparation of nat(and ent)-11α,15-Dihydroxy-9-oxo-15,16-tetramethylene-17,18,19,20-tetranor-13-trans-prostenoic Acid To a solution of 1.01 g of thiophenol in 30 ml of ether under nitrogen at 0° C., is added with stirring, 4.0 ml of 2.3M n-butyllithium. The mixture is stirred for one hour and then a solution of 3.61 g of copper tri-n-butyl phosphine complex in 85 ml of ether is added.

To 2.98 g of 1-(2-trans-iodovinyl)-1-trimethylsilyloxycyclohexane in 8 ml of toluene at −45° C., under nitrogen, is added with stirring 23 ml of 0.8M t-butyllithium. Stirring and cooling are continued for 75 minutes. The cooling bath is removed and the solution is stirred for 10 minutes. Aa 5 ml portion of ether is added and the solution is cooled to −78° C. The copper solution is cooled to −78° C. and then added to the vinyl lithium solution via a double needle. After 30 minutes, a solution of 3.4 g of 1-(6-carbotrimethyl-silyloxyhexyl)-4-trimethylsilyloxycyclopent-2-en-1-one in ether is added. The solution is then placed in a dry ice-acetonitrile bath at −45° C. to −50° C. and stirred for 3 hours. The solution is allowed to warm to −20° C. over 20 minutes and stirred at −20° C. for 10 minutes. To this solution is added 5 ml of acetic acid in 5 ml of ether followed by 0.5M hydrochloric acid. The solution is poured into water and extracted with ether. The ether solution is washed with water and dried with magnesium sulfate. The solvent is removed followed by removal of most of the thiophenol. The residue is dissolved in 100 ml of a mixture of acetic acid, tetrahydrofuran and water and stirred for one hour. The mixture is poured into water and extracted with ether. The ether extract is washed several times with water and dried with magnesium sulfate. The ether is removed leaving a yellow oil. This oil is chromatographed on a dry silica gel column eluting with ether:ethyl acetate 1:1. The product is isolated as a light green-yellow oil which solidifies on drying to give an off-white solid.

EXAMPLE 71

Preparation of nat(and ent)-11α,16-Dihydroxy-9-oxo-16,17-tetramethylene-18,19,20-trinor-5-cis,13-trans-prostadienoic Acid A solution of 10.3 g of 1-(3-tri-n-butylstannyl-2-trans-propenyl)-1-trimethylsilyloxycyclohexane (Ex. 30) in 7 ml of tetrahydrofuran is cooled in a dry ice-acetone bath under nitrogen and treated with 8.6 ml of 2.5M n-butyllithium in hexane during 10 minutes. The resulting solution is stirred at −40° C. for one hour, then at −20° C. to −30° C. for another hour, recooled to −78° C., and treated during 10 minutes with the solution of 2.68 g of copper pentyne, 7.87 ml of hexamethylphosphorus triamide and 19 ml of tetrahydrofuran. The resulting solution is stirred at −70° C. to −50° C. for one hour, recooled to −78° C., and treated with a solution of 5.8 g of 2-(6-carbotrimethylsilyloxyhex-2-cis-enyl)-4-trimethylsilyloxycyclopent-2-en-1-one (Ex. 51) in 12 ml of tetrahydrofuran during 10 minutes. The mixture is then stirred at −40° C. to −50° C. for 40 minutes, then at −20° C. to −25° C. for 25 minutes, recooled to −40° C., and poured into 500 ml of cold, saturated ammonium chloride solution and 300 ml of ether. To the resulting mixture is added 8 ml of glacial acetic acid and it is extracted with ether. The combined ether extract is washed with water, diluted hydrochloric acid, filtered through Celite and washed again with water and saturated sodium chloride solution. Evaporation of the solvents at reduced pressure gives 15.2 g of oil. A solution of this crude oil in 175 ml of glacial acetic acid:tetrahydrofuran:water (4:2:1) is stirred at room temperature under nitrogen for 50 minutes. To the mixture is added 150 ml of toluene and concentrated at reduced pressure. The crude product obtained is purified by chromatography on silica gel to give nat(and ent)-11α,16-dihydroxy-9-oxo-16,17-tetramethylene-18,19,20-trinor-5-cis,-13-trans-prostadienoic acid.

EXAMPLE 72

Preparation of nat-15S,16R(and ent-15R,16S) and nat-15R,16S-(and ent-15S,16R)-11α,15-Dihydroxy-9-oxo-15,16-trimethylene-13-trans-5-cis-prostadienoic Acid To a solution of 1.44 g of thiophenol in 40 ml of ether under nitrogen at 0° C. is added with stirring, 5.65 ml of 2.3M n-butyllithium. After one hour of stirring at 0° C. a solution of bis-tri-n-butylphosphine copper iodide complex in 100 ml of ether is added and the solution is stored overnight in a freezer.

To 4.76 g of 1R,2S(and 1S,2R)-1-(trans-2-iodovinyl)-1-trimethylsilyloxy-2-butylcyclopentone in 10 ml of toluene under nitrogen at −45° C., is added with stirring, 32.5 ml of 0.08M t-butyllithium. After stirring for 90 minutes at −45° C. the solution is removed from the cooling bath and stirred 15 minutes. The solution is cooled to −78° C. The copper solution is cooled to −78° C. and then added to the vinyl lithium solution. After 30 minutes a solution of 4.4 g of 1-(6-carbotrimethylsilyloxyhex-2-cis-enyl)-4-trimethylsilyoxycyclopent-2-en-1-one in 20 ml of ether is added. The solution is stirred at −45° C. for 3 hours and then allowed to warm to −20° C. over a 30 minute period. The solution is stirred at −20° C. for 15 minutes and then a solution of 2.5 ml of acetic acid in 15 ml of ether is added followed by dilute hydrochloric acid. The mixture is extracted with ether. The ether extract is washed with saturated sodium chloride solution and dried with magnesium sulfate. The solvent is removed giving a yellow oil. This oil is stirred in 70 ml of acetic acid:tetrahydrofuran:water (4:2:1) for one hour, poured into water and extracted with ether. The extract is dried with magnesium sulfate and the ether is removed. The residue is chromatographed on a dry columman of silica gel, eluting with ether to give the separated isomers.

EXAMPLE 74-155

In the manner described hereinabove for Examples 69-72, the 9-oxo-prostaglandins shown in Table IV are prepared from the indicated vinyl iodide or vinyl tin compounds and the indicated cyclopent-2-en-1-one. In the reactions involving the 4-hydroxycyclopent-2-en-1-one, these were first converted to their corresponding bis-trimethylsilyloxy derivatives as described hereinabove for Examples 51 and 52. In those cases where two diastereoisomers are formed in the conjugate-addition, only one of the diastereoisomers is listed in Table IV. It should be understood that the other diastereoisomer is also formed which in its nat and ent forms has an opposite (mirror image) configuration at the assymmetric carbon atoms on the β-chain (the chain containing $C_{13}$ ... $C_{14}$ etc.) to that of the respective nat and ent forms of the listed diastereoisomer; both of these diastereoisomers are claimed in this invention as well as their component enantiomers.

Table IV

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 74 | 29a | 2-(6-carboxyhexyl)-4-hydroxycyclopent-2-en-1-one | nat-15S,16R-(and ent-15R,16S)-11α,15-dihydroxy-9-oxo-15,16-trimethylene-13-trans-prostenoic acid |
| 75 | 36 | 2-(6-carboxyhexyl)-4-hydroxycyclopent-2-en-1-one | nat-15S,16S-(and ent-15R,16R)-11α,15-dihydroxy-9-oxo-15,16-trimethylene-13-trans-prostenoic acid |
| 76 | 31 | 2-(6-carboxyhexyl)-4-hy- | nat-(and ent)-11α,15-dihydroxy-9- |

Table IV-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | droxycyclopent-2-en-1-one | oxo-15,16-tetramethylene-17,18,19,-20-tetranor-13-trans-prostenoic acid |
| 77 | 32 | 2-(6-carboxyhexyl)-4-hydroxycyclopent-2-en-1-one | nat-(and ent)-11α,15-dihydroxy-9-oxo-15,16-trimethylene-17,18,19,20-tetranor-13-trans-prostenoic acid |
| 78 | 33 | 2-(6-carboxyhexyl)-4-hydroxycyclopent-2-en-1-one | nat-(and ent)-11α,15-dihyroxy-15-16-pentamethylene-17,18,19,20-tetranor-13-trans-prostenoic acid |
| 79 | 34 | 2-(6-carboxyhexyl)-4-hydroxycyclopent-2-en-1-one | nat-15S,17R-(and ent-15R,17S)-11α,-15-dihydroxy-9-oxo-15,17-dimethylene-13-trans-prostenoic acid |
| 80 | 35 | 2-(6-carboxyhexyl)-4-hydroxycyclopent-2-en-1-one | nat-15S,17S-(and ent-15R,17R)-11α,-15-dihydroxy-9-oxo-15,17-dimethylene-13-trans-prostenoic acid |
| 81 | 37 | 2-(6-carboxyhexyl)-4-hydroxycyclopent-2-en-1-one | nat-15S,16R-(and ent-15R,16S)-11α,-15-dihydroxy-9-oxo-15,16-tetramethylene-13-trans-prostenoic acid |
| 82 | 38 | 2-(6-carboxyhexyl)-4-hydroxycyclopent-2-en-1-one | nat-15S,16S-(and ent-15R,16R)-11α,-15-dihydroxy-9-oxo-15,16-tetramethylene-13-trans-prostenoic acid |
| 83 | 39 | 2-(6-carboxyhexyl)-4-hydroxycyclopent-2-en-1-one | nat-15R,16S-(and ent-15S,16R)-11α,-15-dihydroxy-9-oxo-15,16-trimethylene-16-(3-trifluoromethylphenoxy)-17,18,19,20-tetranor-13-trans-prostenoic acid |
| 84 | 40 | 2-(6-carboxyhexyl)-4-hydroxycyclopent-2-en-1-one | nat-15R,16R-(and ent-15S,16S)-11α,-15-dihydroxy-9-oxo-15,16-trimethylene-16-(3-trifluoromethylphenoxy)-17,18,19,20-tetranor-13-trans-prostenoic acid |
| 85 | 30 | 2-(6-carboxyhexyl)-4-hydroxycyclopent-2-en-1-one | nat-(and ent)-11α,16-dihydroxy-9-oxo-16,17-tetramethylene-18,19,20-trinor-13-trans-prostenoic acid |
| 86 | 41 | 2-(6-carboxyhexyl)-4-hydroxycyclopent-2-en-1-one | nat-15R,16S-(and ent-15S,16R)-11α,-15-dihydroxy-9-oxo-15,16-trimethylene-16-(4-fluorophenoxy(-17,18,19,-20-tetranor-13-trans-prostenoic acid |
| 87 | 42 | 2-(6-carboxyhexyl)-4-hydroxycyclopent-2-en-1-one | nat-15R,16R-(and ent-15S,16S)-11α,-15-dihydroxy-9-oxo-15,16-trimethylene-16-(4-fluorophenoxy)-17,18,19,-20-tetranor-13-trans-prostenoic acid |
| 88 | 43 | 2-(6-carboxyhexyl)-4-hydroxycyclopent-2-en-1-one | nat-15R,16S-(and ent-15S,16R)-11α,-15-dihydroxy-9-oxo-15,16-trimethylene-16-(3-chlorophenoxy)-17,18,19,-20-tetranor-13-trans-prostenoic acid |
| 89 | 44 | 2-(6-carboxyhexyl)-4-hydroxycyclopent-2-en-1-one | nat-15R,16R-(and ent-15S,16S)-11α,-15-dihydroxy-9-oxo-15,16-trimethylene-16-(3-chlorophenoxy)-17,18,19,-20-tetranor-13-trans-prostenoic acid |
| 90 | 45 | 2-(6-carboxyhexyl)-4-hydroxycyclopent-2-en-1-one | nat-15S,17R-(and ent-15R,17S)-11α,-15-dihydroxy-9-oxo-15,17-trimethylene-19,20-dinor-13-trans-prostenoic acid |
| 91 | 46 | 2-(6-carboxyhexyl)-4-hydroxycyclopent-2-en-1-one | nat-15S,17S-(and ent-15R,17R)-11α,-15-dihydroxy-9-oxo-15,17-trimethylene-19,20-dinor-13-trans-prostenoic acid |
| 92 | 47 | 2-(6-carboxyhexyl)-4-hydroxycyclopent-2-en-1-one | nat-16R,17S-(and ent-16S,17R)-11α,-16-dihydroxy-9-oxo-16,17-trimethylene-20-methyl-13-trans-prostenoic acid |
| 93 | 48 | 2-(6-carboxyhexyl)-4-hydroxycyclopent-2-en-1-one | nat-16R,17R-(and ent-16S,17S)-11α,-16-dihydroxy-9-oxo-16,17-trimethylene-20-methyl-13-trans-prostenoic acid |
| 94 | 49 | 2-(6-carboxyhexyl)-4-hydroxycyclopent-2-en-1-one | nat-16R,17S-(and ent-16S,17R)-11α,-16-dihydroxy-9-oxo-16,17-trimethylene-16-(3-trifluoromethylphenoxy)-18,19,20-trinor-13-trans-prostenoic acid |
| 95 | 50 | 2-(6-carboxyhexyl)-4-hydroxycyclopent-2-en-1-one | nat-16R,17R-(and ent-16S,17S)-11α,-16-dihydroxy-9-oxo-16,17-trimethylene-16-(3-trifluoromethylphenoxy)-18,19,20-trinor-13-trans-prostenoic acid |
| 96 | 29a | 2-(5-carboxypentyl)-4-hydroxycyclopent-2-en-1-one | nat-15S,16R-(and ent-15R,16S)-11α,-15-dihydroxy-9-oxo-15,16-trimethylene-2-nor-13-trans-prostenoic acid |
| 97 | 36 | 2-(5-carboxypentyl)-4-hy- | nat-15S,16S-(and ent-15R,16R)-11α,- |

Table IV-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | droxycyclopent-2-en-1-one | 15-dihydroxy-9-oxo-15,16-trimethylene-2-nor-13-trans-prostenoic acid |
| 98 | 31 | 2-(5-carboxypentyl)-4-hydroxycyclopent-2-en-1-one | nat-(and ent)-11α,15-dihydroxy-9-oxo-15,16-tetramethylene-,17,18,-19,20-pentanor-13-trans-prostenoic acid |
| 99 | 32 | 2-(5-carboxypentyl)-4-hydroxycyclopent-2-en-1-one | nat-(and ent)-11α,15-dihydroxy-9-oxo-15,16-trimethylene-2,17,18,-19,20-pentanor-13-trans-prostenoic acid |
| 100 | 33 | 2-(5-carboxypentyl)-4-hydroxycyclopent-2-en-1-one | nat-(and ent)-11α,15-dihydroxy-9-oxo-15,16-pentamethylene-2,17,18,-19,20-pentanor-13-trans-prostenoic acid |
| 101 | 34 | 2-(5-carboxypentyl)-4-hydroxycyclopent-2-en-1-one | nat-15S,17R-(and ent-15R,17S)-11α,-15-dihydroxy-9-oxo-15,17-dimethylene-2-nor-13-trans-prostenoic acid |
| 102 | 35 | 2-(5-carboxypentyl)-4-hydroxycyclopent-2-en-1-one | nat-15S,17S-(and ent-15R,17R)-11α,-15-dihydroxy-9-oxo-15,17-dimethylene-2-nor-13-trans-prostenoic acid |
| 103 | 39 | 2-(5-carboxypentyl)-4-hydroxycyclopent-2-en-1-one | nat-15R,16S-(and ent-15S,16R)-11α,-15-dihydroxy--oxo-15,16-trimethylene-16-(3-trifluoromethylphenoxy)-7,17,18,19,20-pentanor-13-trans-prostenoic acid |
| 104 | 40 | 2-(5-carboxypentyl)-4-hydroxycyclopent-2-en-1-one | nat-15R,16R-(and ent-15S,16S)-11α,-15-dihydroxy--oxo-15,16-trimethylene-16-(3-trifluoromethylphenoxy)-2,17,18,19,20-pentanor-13-trans-prostenoic acid |
| 105 | 29a | 2-(7-carboxyheptyl)-4-hydroxycyclopent-2-en-1-one | nat-15S,16R-(and ent-15R,16S)-11α,-15-dihydroxy-9-oxo-15,16-trimethylene-1-homo-13-trans-prostenoic acid |
| 106 | 36 | 2-(7-carboxyheptyl)-4-hydroxycyclopent-2-en-1-one | nat-15S,16S-(and ent-15R,16R)-11α,-15-dihydroxy-9-oxo-15,16-trimethylene-1-homo-13-trans-prostenoic acid |
| 107 | 31 | 2-(7-carboxyheptyl)-4-hydroxycyclopent-2-en-1-one | nat-(and ent)-11α,15-dihydroxy-9-oxo-15,16-tetramethylene-17,18,19,-20-tetranor-1-homo-13-trans-prostenoic acid |
| 108 | 37 | 2-(7-carboxyheptyl)-4-hydroxycyclopent-2-en-1-one | nat-15S,16R-(and ent-15R,16S)-11α,-15-dihydroxy-9-oxo-15,16-tetramethylene-1-homo-13-trans-prostenoic acid |
| 109 | 38 | 2-(7-carboxyheptyl)-4-hydroxycyclopent-2-en-1-one | nat-15S,16S-(and ent-15R,16R)-11α,-15-dihydroxy-9-oxo-15,16-tetramethylene-1-homo-13-trans-prostenoic acid |
| 110 | 41 | 2-(7-carboxyheptyl)-4-hydroxycyclopent-2-en-1-one | nat-15R,16S-(and ent-15S,16R)-11α,-15-dihydroxy-9-oxo-15,16-trimethylene-16-(4-fluorophenoxy)-1-homo-17,18,19,20-tetranor-13-trans-prostenoic acid |
| 111 | 42 | 2-(7-carboxyheptyl)-4-hydroxycyclopent-2-en-1-one | nat-15R,16R-(and ent-15S,16S)-11α,-15-dihydroxy-9-oxo-15,16-trimethylene-16-(4-fluorophenoxy)-1-homo-17,18,19,20-tetranor-13-trans-prostenoic acid |
| 112 | 45 | 2-(8-carboxyoctyl)-4-hydroxycyclopent-2-en-1-one | nat-15S,17R-(and ent-15R,17S)-11α,-15-dihydroxy-9-oxo-15,17-trimethylene-19,20-dinor-1a,1b-dihomo-13-trans-prostenoic acid |
| 113 | 46 | 2-(8-carboxyoctyl)-4-hydroxycyclopent-2-en-1-one | nat-15S,17S-(and ent-15R,17R)-11α,-15-dihydroxy-9-oxo-15,17-trimethylene-19,20-dinor-1a,1b-dihomo-13-trans-prostenoic acid |
| 114 | 47 | 2-(8-carboxyoctyl)-4-hydroxycyclopent-2-en-1-one | nat-16R,17S-(and ent-16S,17R)-11α,-16-dihydroxy-9-oxo-16,17-trimethylene-20-methyl-1a,1b-dihomo-13-trans-prostenoic acid |
| 115 | 48 | 2-(8-carboxyoctyl)-4-hydroxycyclopent-2-en-1-one | nat-16R,17R-(and ent-16S,17S)-11α,-16-dihydroxy-9-oxo-16,17-trimethylene-20-methyl-1a,1b-dihomo-13-trans-prostenoic acid |
| 116 | 49 | 2-(8-carboxyoctyl)-4-hydroxycyclopent-2-en-1-one | nat-16R,17S-(and ent-16S,17R)-11α,-16-dihydroxy-9-oxo-16,17-trimethylene-16-(3-trifluoromethylphenoxy)-18,19,20-trinor-1a,1b-dihomo-13-trans-prostenoic acid |
| 117 | 50 | 2-(8-carboxyoctyl)-4-hydroxycyclopent-2-en-1-one | nat-16R,17R-(and ent-16S,17S)-11α,-16-dihydroxy-9-oxo-16,17-trimethy- |

Table IV-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | | lene-16-(3-trifluoromethylphenoxy)-18,19,20-trinor-1a,1b-dihomo-13-trans-prostenoic acid |
| 118 | 29a | 2-(6-carboxyhex-2-cis-enyl)-4-hydroxycyclo-pent-2-en-1-one | nat-15S,16R-(and ent-15R,16S)-11α,-15-dihydroxy-9-oxo-15,16-trimethylene-13-trans-5-cis-prostadienoic acid |
| 119 | 36 | 2-(6-carboxyhex-2-cis-enyl)-4-hydroxycyclo-pent-2-en-1-one | nat-15S,16S-(and ent-15R,16R)-11α,-15-dihydroxy-9-oxo-15,16-trimethylene-13-trans-5-cis-prostadienoic acid |
| 120 | 32 | 2-(6-carboxyhex-2-cis-enyl)-4-hydroxycyclo-pent-2-en-1-one | nat-(and ent)-11α,15-dihydroxy-9-oxo-15,16-trimethylene-17,18,19,-20-tetranor-13-trans-5-cis-prostadienoic acid |
| 121 | 33 | 2-(6-carboxyhex-2-cis-enyl)-4-hydroxycyclo-pent-2-en-1-one | nat-(and ent)-11α,15-dihydroxy-9-oxo-15,16-pentamethylene-17,18,-19,20-tetranor-13-trans-5-cis-prostadienoic acid |
| 122 | 34 | 2-(6-carboxyhex-2-cis-enyl)-4-hydroxycyclo-pent-2-en-1-one | nat-15S,17R-(and ent-15R,17S)-11α,-15-dihydroxy-9-oxo-15,17-dimethylene-13-trans-5-cis-prostadienoic acid |
| 123 | 35 | 2-(6-carboxyhex-2-cis-enyl)-4-hydroxycyclo-pent-2-en-1-one | nat-15S,17S-(and ent-15R,17R)-11α,-15-dihydroxy-9-oxo-15,17-dimethylene-13-trans-5-cis-prostadienoic acid |
| 124 | 37 | 2-(6-carboxyhex-2-cis-enyl)-4-hydroxycyclo-pent-2-en-1-one | nat-15S,16R-(and ent-15R,16S)-11α,-15-dihydroxy-9-oxo-15,16-tetramethylene-13-trans-5-cis-prostadienoic acid |
| 125 | 38 | 2-(6-carboxyhex-2-cis-enyl)-4-hydroxycyclo-pent-2-en-1-one | nat-15S,16S-(and ent-15R,16R)-11α,-15-dihydroxy-9-oxo-15,16-tetramethylene-13-trans-5-cis-prostadienoic acid |
| 126 | 39 | 2-(6-carboxyhex-2-cis-enyl)-4-hydroxycyclo-pent-2-en-1-one | nat-15R,16S-(and ent-15S,15R)-11α,-15-dihydroxy-9-oxo-15,16-trimethylene-16-(3-trifluoromethylphenoxy)-17,18,19,20-tetranor-13-trans-5-cis-prostadienoic acid |
| 127 | 40 | 2-(6-carboxyhex-2-cis-enyl)-4-hydroxycyclo-pent-2-en-1-one | nat-15R,16R-(and ent-15S,16S)-11α,-15-dihydroxy-9-oxo-15,16-trimethylene-16-(3-trifluoromethylphenoxy)-17,18,19,20-tetranor-13-trans-5-cis-prostadienoic acid |
| 128 | 41 | 2-(6-carboxyhex-2-cis-enyl)-4-hydroxycyclo-pent-2-en-1-one | nat-15R,16S-(and ent-15S,16R)-11α,-15-dihydroxy-9-oxo-15,16-trimethylene-16-(4-fluorophenoxy)-17,18,19,-20-tetranor-13-trans-5-cis-prostadienoic acid |
| 129 | 42 | 2-(6-carboxyhex-2-cis-enyl)-4-hydroxycyclo-pent-2-en-1-one | nat-15R,16R-(and ent-15S,16S)-11α,-15-dihydroxy-9-oxo-15,16-trimethylene-16-(4-fluorophenoxy)-17,18,19,-20-tetranor-13-trans-5-cis-prostadienoic acid |
| 130 | 43 | 2-(6-carboxyhex-2-cis-enyl)-4-hydroxycyclo-pent-2-en-1-one | nat-15R,16S-(and ent-15S,16R)-11α,-15-dihydroxy-9-oxo-15,16-trimethylene-16-(3-chlorophenoxy)-17,18,-19,20-tetranor-13-trans-5-cis-prostadienoic acid |
| 131 | 44 | 2-(6-carboxyhex-2-cis-enyl)-4-hydroxycyclo-pent-2-en-1-one | nat-15R,16R-(and ent-15S,16S)-11α,-15-dihydroxy-9-oxo-15,16-trimethylene-16-(3-chlorophenoxy)-17,18,-19,20-tetranor-13-trans-5-cis-prostadienoic acid |
| 132 | 45 | 2-(6-carboxyhex-2-cis-enyl)-4-hydroxycyclo-pent-2-en-1-one | nat-15S,17R-(and ent-15R,17S)-11α,-15-dihydroxy-9-oxo-15,17-trimethylene-19,20-dinor-13-trans-5-cis-prostadienoic acid |
| 133 | 46 | 2-(6-carboxyhex-2-cis-enyl)-4-hydroxycyclo-pent-2-en-1-one | nat-15S,17S-(and ent-15R,17R)-11α,-15-dihydroxy-9-oxo-15,17-trimethylene-19,20-dinor-13-trans-5-cis-prostadienoic acid |
| 134 | 47 | 2-(6-carboxyhex-2-cis-enyl)-4-hydroxycyclo-pent-2-en-1-one | nat-16R,17S-(and ent-16S,17R)-11α,-16-dihydroxy-9-oxo-16,17-trimethylene-20-methyl-13-trans-5-cis-prostadienoic acid |
| 135 | 48 | 2-(6-carboxyhex-2-cis- | nat-16R,17R-(and ent-16S,17S)-11α,- |

Table IV-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | enyl)-4-hydroxycyclopent-2-en-1-one | 16-dihydroxy-9-oxo-16,17-trimethylene-20-methyl-13-trans-5-cis-prostadienoic acid |
| 136 | 49 | 2-(6-carboxyhex-2-cis-enyl)-4-hydroxycyclopent-2-en-1-one | nat-16R,17S-(and ent-16S,17R)-11α,-16-dihydroxy-9-oxo-16,17-trimethylene-17-(3-trifluoromethylphenoxy)-18,19,20-trinor-13-trans-5-cis-prostadienoic acid |
| 137 | 50 | 2-(6-carboxyhex-2-cis-enyl)-4-hydroxycyclopent-2-en-1-one | nat-16R,17R-(and ent-16S,17S)-11α,-16-dihydroxy-9-oxo-16,17-trimethylene-17-(3-trifluoromethylphenoxy)-18,19,20-trinor-13-trans-5-cis-prostadienoic acid |
| 138 | 29a | 2-(8-carboxyoct-2-cis-enyl)-4-hydroxycyclopent-2-en-1-one | nat-15S,16R-(and ent-15R,16S)-11α,-15-dihydroxy-9-oxo-15,16-trimethylene-1a,1b-dihomo-13-trans-5-cis-prostadienoic acid |
| 139 | 36 | 2-(8-carboxyoct-2-cis-enyl)-4-hydroxycyclopent-2-en-1-one | nat-15S,16S-(and ent-15R,16R)-11α,-15-dihydroxy-9-oxo-15,16-trimethylene-1a,1b-dihomo-13-trans-5-cis-prostadienoic acid |
| 140 | 31 | 2-(8-carboxyoct-2-cis-enyl)-4-hydroxycyclopent-2-en-1-one | nat-(and ent)-11α,15-dihydroxy-9-oxo-15,16-tetramethylene-1a,1b-dihomo-17,18,19,20-tetranor-13-trans-5-cis-prostadienoic acid |
| 141 | 37 | 2-(8-carboxyoct-2-cis-enyl)-4-hydroxycyclopent-2-en-1-one | nat-15S,16R-(and ent-15R,16S)-11α,-15-dihydroxy-9-oxo-15,16-tetramethylene-1a,1b-dihomo-13-trans-5-cis-prostadienoic acid |
| 142 | 38 | 2-(8-carboxyoct-2-cis-enyl)-4-hydroxycyclopent-2-en-1-one | nat-15S,16S-(and ent-15R,16R)-11α,-15-hydroxy-9-oxo-15,16-tetramethylene-1a,1b-dihomo-13-trans-5-cis-prostadienoic acid |
| 143 | 39 | 2-(8-carboxyoct-2-cis-enyl)-4-hydroxycyclopent-2-en-1-one | nat-15R,16S-(and ent-15S,16R)-11α,-15-dihydroxy-9-oxo-15,16-trimethylene-16-(3-trifluoromethylphenoxy)-1a,1b-dihomo-17,18,19,20-tetranor-13-trans-5-cis-prostadienoic acid |
| 144 | 40 | 2-(8-carboxyoct-2-cis-enyl)-4-hydroxycyclopent-2-en-1-one | nat-15R,16R-(and ent-15S,16S)-11α,-15-dihydroxy-9-oxo-15,16-trimethylene-16-(3-trifluoromethylphenoxy)-1a,1b-dihomo-17,18,19,20-tetranor-13-trans-5-cis-prostadienoic acid |
| 145 | 29a | 2-(6-carboxy-5-oxa-hexyl)-4-hydroxycyclopent-2-en-1-one | nat-15S,16R-(and ent-15R,16S)-11α,-15-dihydroxy-3-oxa-9-oxo-15,16-trimethylene-13-trans-prostenoic acid |
| 146 | 36 | 2-(6-carboxy-5-oxa-hexyl)-4-hydroxycyclopent-2-en-1-one | nat-15S,16S-(and ent-15R,16R)-11α,-15-dihydroxy-3-oxa-9-oxo-15,16-trimethylene-13-trans-prostenoic acid |
| 147 | 31 | 2-(6-carboxy-5-oxa-hexyl)-4-hydroxycyclopent-2-en-1-one | nat-(and ent)-11α,15-dihydroxy-3-oxa-9-oxo-15,16-tetramethylene-17,18,19,20-tetranor-13-trans-prostenoic acid |
| 148 | 43 | 2-(6-carboxy-4-methyl-hex-2-cis-enyl)-4-hydroxy-cyclopent-2-en-1-one | nat-15R,16S-(and ent-15S,16R)-11α,-15-dihydroxy-4-methyl-9-oxo-15,16-trimethylene-16-(3-chlorophenoxy)-17,18,19,20-tetranor-13-trans-prostenoic acid |
| 149 | 44 | 2-(6-carboxy-4-methyl-hex-2-cis-enyl)-4-hydroxy-cyclopent-2-en-1-one | nat-15R,16R-(and ent-15S,16S)-11α,-15-dihydroxy-4-methyl-9-oxo-15,16-trimethylene-16-(3-chlorophenoxy)-17,18,19,20-tetranor-13-trans-prostenoic acid |
| 150 | 45 | 2-(6-carboxy-4-methyl-hex-2-cis-enyl)-4-hydroxy-cyclopent-2-en-1-one | nat-15S,17R-(and ent-15R,17S)-11α,-15-dihydroxy-4-methyl-9-oxo-15,17-trimethylene-19,20-dinor-13-trans-prostenoic acid |
| 151 | 46 | 2-(6-carboxy-4-methyl-hex-2-cis-enyl)-4-hydroxy-cyclopent-2-en-1-one | nat-15S,17S-(and ent-15R,17R)-11α,-15-dihydroxy-4-methyl-9-oxo-15,17-trimethylene-19,20-dinor-13-trans-prostenoic acid |
| 152 | 47 | 2-(6-carboxy-4-methyl-hex-2-cis-enyl)-4-hydroxy-cyclopent-2-en-1-one | nat-16R,17S-(and ent-16S,17R)-11α,-16-dihydroxy-4-methyl-9-oxo-16,17-trimethylene-20-methyl-13-trans-prostenoic acid |
| 153 | 48 | 2-(6-carboxy-4-ethylhex-2-cis-enyl)-4-hydroxy-cyclopent-2-en-1-one | nat-16R,17R-(and ent-16S,17S)-11α,-16-dihydroxy-4-ethyl-9-oxo-16,17-trimethylene-20-methyl-13-trans-prostenoic acid |

Table IV-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 154 | 49 | 2-(6-carboxy-4 ethylhex-2-cis-enyl)-4-hydroxy-cyclopent-2-en-1-one | nat-16R,17S-(and ent-16S,17R)-11α,16-dihydroxy-4-ethyl-9-oxo-15,17-trimethylene-17-(3-trifluoromethylphenoxy)-18,19,20-trinor-13-trans-prostenoic acid |
| 155 | 50 | 2-(6-carboxy-4-ethylhex-2-cis-enyl)-4-hydroxy-cyclopent-2-en-1-one | nat-16R,17R-(and ent-16S,17S)-11α,16-dihydroxy-4-ethyl-9-oxo-15,17-trimethylene-17-(3-trifluoromethylphenoxy)-18,19,20-trinor-13-trans-prostenoic acid |

EXAMPLES 156–173

In the manner of Examples 69–72, the 9-oxo-11α-hydroxy prostaglandin methyl esters listed in Table V are prepared from the indicated cyclopent-2-en-1-one and vinyl iodide or vinyl tin compound indicated.

In those cases where two diastereoisomers are formed in the conjugate-addition both are obtained in an optically active form and only one of the diastereoisomers is listed in Table V. It should be understood that the other diastereoisomer is also formed which in its nat or ent forms has an opposite (mirror image) configuration at the assymmetric carbon atoms on the β-chain (the chain containing $C_{13}$–$C_{14}$ ... etc.) to that of the respective nat or ent forms of the listed diastereoisomer; both of these diastereoisomers are claimed in this invention.

Table V

| Example | Vinyl Iodide or Vinyl Tin of Example | Cyclopent-2-en-1-one | Product optically active 9-oxo-prostaglandin and its optically active diastereoisomer |
|---|---|---|---|
| 156 | 29a | 2-(6-carbomethoxyhexyl)-4(R)-trimethylsilyloxy-cyclopent-2-en-1-one | nat-methyl-15S,16R-11α,15-dihydroxy-9-oxo-15,16-trimethylene-13-trans-prostenoate |
| 157 | 36 | 2-(6-carbomethoxyhexyl)-4(R)-trimethylsilyloxy-cyclopent-2-en-1-one | nat-methyl-15S,16S-11α,15-dihydroxy-9-oxo-15,16-trimethylene-13-trans-prostenoate |
| 158 | 31 | 2-(6-carbomethoxyhexyl)-4(R)-trimethylsilyloxy-cyclopent-2-en-1-one | nat-methyl-11α,15-dihydroxy-9-oxo-15,16-tetramethylene-17,18,19,20-tetranor-13-trans-prostenoate |
| 159 | 30 | 2-(6-carbomethoxyhexyl)-4(R)-trimethylsilyloxy-cyclopent-2-en-1-one | nat-methyl-11α,16-dihydroxy-9-oxo-16,17-tetramethylene-18,19,20-trinor-13-trans-prostenoate |
| 160 | 39 | 2-(6-carbomethoxyhexyl)-4(R)-trimethylsilyloxy-cyclopent-2-en-1-one | nat-methyl-15R,16S-11α,15-dihydroxy-9-oxo-15,16-trimethylene-16-(3-trifluoromethylphenoxy)-17,18,19,20-tetranor-13-trans-prostenoate |
| 161 | 40 | 2-(6-carbomethoxyhexyl)-4(R)-trimethylsilyloxy-cyclopent-2-en-1-one | nat-methyl-15R,16R-11α,15-dihydroxy-9-oxo-15,16-trimethylene-16-(3-trifluoromethylphenoxy)-17,18,19,20-tetranor-13-trans-prostenoate |
| 162 | 29a | 2-(6-carbomethoxyhexyl)-4(S)-trimethylsilyloxy-cyclopent-2-en-1-one | ent-methyl-15R,16S-11α,15-dihydroxy-9-oxo-15,16-trimethylene-13-trans-prostenoate |
| 163 | 36 | 2-(6-carbomethoxyhexyl)-4(S)-trimethylsilyloxy-cyclopent-2-en-1-one | ent-methyl-15R,16R-11α,15-dihydroxy-9-oxo-15,16-trimethylene-13-trans-prostenoate |
| 164 | 31 | 2-(6-carbomethoxyhexyl)-4(S)-trimethylsilyloxy-cyclopent-2-en-1-one | ent-methyl-11α,15-dihydroxy-9-oxo-15,16-tetramethylene-17,18,19,20-tetranor-13-trans-prostenoate |
| 165 | 30 | 2-(6-carbomethoxyhexyl)-4(S)-trimethylsilyloxy-cyclopent-2-en-1-one | ent-methyl-11α,16-dihydroxy-9-oxo-16,17-tetramethylene-18,19,20-trinor-13-trans-prostenoate |
| 166 | 39 | 2-(6-carbomethoxyhexyl)-4(S)-trimethylsilyloxy-cyclopent-2-en-1-one | ent-methyl-15S,16R-11α,15-dihydroxy-9-oxo-15,16-trimethylene-16-(3-trifluoromethylphenoxy)-17,18,19,20-tetranor-13-trans-prostenoate |
| 167 | 40 | 2-(6-carbomethoxyhexyl)-4(S)-trimethylsilyloxy-cyclopent-2-en-1-one | ent-methyl-15S,16S-11α,15-dihydroxy-9-oxo-15,16-trimethylene-16-(3-trifluoromethylphenoxy)-17,18,19,20-tetranor-13-trans-prostenoate |
| 168 | 29a | 2-(6-carbomethoxyhex-2-cis-enyl)-4(R)-trimethylsilyloxycyclopent-2-en-1- | nat-methyl-15S,16R-11α,15-dihydroxy-9-oxo-15,16-trimethylene-13-trans-5-cis-prostenoate |

Table V-continued

| Example | Vinyl Iodide or Vinyl Tin of Example | Cyclopent-2-en-1-one | Product optically active 9-oxo-prostaglandin and its optically active diastereoisomer |
|---|---|---|---|
| 169 | 36 | 2-(6-carbomethoxyhex-2-cis-enyl)-4-(R)-trimethyl-silyloxycyclopent-2-en-1-one | nat-methyl-15S,16S-11α,15-dihydroxy-9-oxo-15,16-trimethylene-13-trans-5-cis-prostadienoate |
| 170 | 31 | 2-(6-carbomethoxyhex-2-cis-enyl-4(R)-trimethyl-silyloxycyclopent-2-en-1-one | nat-methyl-11α,15-dihydroxy-9-oxo-15,16-tetramethylene-17,18,19,20-tetranor-13-trans-5-cis-prostadienoate |

| Example | Vinyl Iodide or Vinyl Tin of Example | Cyclopent-2-en-1-one | Product optically active 9-oxo-prostaglandin and its optically active diastereoisomer |
|---|---|---|---|
| 171 | 30 | 2-(6-carbomethoxyhex-2-cis-enyl)-4-(R)-trimethyl-silyloxycyclopent-2-en-1-one | nat-methyl-11α,16-dihydroxy-9-oxo-16,17-tetramethylene-18,19,20-trinor-13-trans-5-cis-prostadienoate |
| 172 | 39 | 2-(6-carbomethoxyhex-2-cis-enyl)-4(R)-trimethyl-silyloxycyclopent-2-en-1-one | nat-methyl-15R,16S-11α,15-dihydroxy-9-oxo-15,16-trimethylene-16-(3-trifluoromethylphenoxy)-17,18,19,20-tetranor-13-trans-5-cis-prostadienoate |
| 173 | 40 | 2-(6-carbomethoxyhex-2-cis-enyl)-4(R)-trimethyl-silyloxycyclopent-2-en-1-one | nat-methyl-15R,16R-11α,15-dihydroxy-9-oxo-15,16-trimethylene-16-(3-trifluoromethylphenoxy)-17,18,19,20-tetranor-13-trans-5-cis-prostadienoate |

| Example | Vinyl Iodide or Vinyl Tin of Example | Cyclopent-2-en-1-one | Product 9-oxo-prostaglandin and its diastereoisomer |
|---|---|---|---|
| 174 | 31 | 2-(6-carbotrimethylsilyloxy-5-thiahexyl)-4-trimethylsilyloxycyclopent-2-en-1-one | nat-(and ent)-11α,15-dihydroxy-3-thia-9-oxo-15,16-trimethylene-17,18,19,20-tetranor-13-trans-prostenoic acid |
| 175 | 29a | 2-(6-carbotrimethylsilyloxy-5-thiahexyl)-4-trimethylsilyloxycyclopent-2-en-1-one | nat-15S,16R(and ent-15R, 16S)-11α,15-dihydroxy-3-thia-9-oxo-15,16-trimethylene-13-trans-prostenoic acid |
| 176 | 36 | 2-(6-carbotrimethylsilyl)-oxy-5-thiahexyl)-4-trimethylsilyloxycyclopent-2-en-1-one | nat-15S,16S-(and ent-15R,16R)-11α,-15-dihydroxy-3-thia-9-oxo-15,16-trimethylene-13-trans-prostenoic acid |
| 177 | 30 | 2-(6-carbotrimethylsilyloxy-5-thiahexyl)-4-trimethylsilyloxycyclopent-2-en-1-one | nat-(and ent)-11α,16-dihydroxy-3-thia-9-oxo-16,17-tetramethylene-18,19,20-trinor-13-trans-prostenoic acid |

| Example | Vinyl Iodide or Vinyl Tin of Example | Cyclopent-2-en-1-one | Product 9-oxo-prostaglandin and its diastereoisomer |
|---|---|---|---|
| 178 | 39 | 2-(6-carbotrimethylsilyloxy-5-thiahexyl)-4-trimethylsilyloxycyclopent-2-en-1-one | nat-15R,16S-(and ent-15S,16R)-11α,-15-dihydroxy-3-thia-9-oxo-15,16-trimethylene-16-(3-trifluoromethylphenoxy)-17,18,19,20-tetranor-13-trans-prostenoic acid |
| 179 | 40 | 2-(6-carbotrimethylsilyloxy-5-triahexyl)-4-trimethylsilyloxycyclopent-2-en-1-one | nat-15R,16R-(and ent-15S,16S)-11α,-15-dihydroxy-3-thia-9-oxo-15,16-trimethylene-16-(3-trifluoromethylphenoxy)-17,18,19,20-tetranor-13-trans-prostenoic acid |
| 180 | 31 | 2-(5-carbotrimethylsilyloxy-4-thiapentyl)-4-trimethylsilyloxycyclopent-2-en-1-one | nat-(and ent)-11α,15-dihydroxy-3-thia-9-oxo-15,16-tetramethylene-4,17,18,19,20-pentanor-13-trans-prostenoic acid |
| 181 | 29a | 2-(5-carbotrimethylsilyloxy-4-thiapentyl)-4-trimethylsilyloxycyclopent-2-en-1-one | nat-15S,16R-(and ent-15R,16S)-11α,-15-dihydroxy-3-thia-9-oxo-15,16-trimethylene-4-nor-13-trans-prostenoic acid |

| Example | Vinyl Iodide or Vinyl Tin of Example | Cyclopent-2-en-1-one | Product 9-oxo-prostaglandin and its diastereoisomer |
|---|---|---|---|
| 182 | 36 | 2-(5-carbotrimethylsilyloxy-4-thiapentyl)-4-trimethylsilyloxycyclopent-2-en-1-one | nat-15S,16S-(and ent-15R,16R)-11α,-15-dihydroxy-3-thia-9-oxo-15,16-trimethylene-4-nor-13-trans-prostenoic acid |
| 183 | 30 | 2-(5-carbotrimethylsilyloxy-4-thiapentyl)-4-trimethylsilyloxycyclopent-2-en-1-one | nat-(and ent)-11α,16-dihydroxy-3-thia-9-oxo-16,17-tetramethylene-4,-18,19,20-tetranor-13-trans-prostenoic acid |
| 184 | 39 | 2-(5-carbotrimethylsilyloxy-4-thiapentyl)-4-trimethylsilyloxycyclopent-2-en-1-one | nat-15R,16S-(and ent-15S,16R)-11α,-15-dihydroxy-3-thia-9-oxo-15,16-trimethylene-16-(3-trifluoromethylphenoxy)-4,17,18,19,20-pentanor-13- |

Table V-continued

| | | | |
|---|---|---|---|
| 185 | 40 | 2-(5-carbotrimethylsilyl-oxy-4-thiapentyl)-4-tri-methylsilyloxycyclopent-2-en-1-one | trans-prostenoic acid nat-15R,16R-(and ent-15S,16S)-11α,-15-dihydroxy-3-thia-9-oxo-15,16-tri-methylene-16-(3-trifluoromethyl-phenoxy)-4,17,18,19,20-pentanor-13-trans-prostenoic acid |

EXAMPLE 186

Preparation of methyl nat(and ent)-11α,15-dihydroxy-9-oxo-15,16-tetramethylene-17,18,19,20-tetranor-5-cis-13-transprostadienoate To an ethereal solution of 0.10 g of nat(and ent)-11α,15-dihydroxy-9-oxo-15,16-tetramethylene-17,18,19,20-tetranor-5-cis-13-trans-prostadienoic acid is added an excess of ethereal diazomethane. After 5 minutes the excess diazomethane and the solvent is blown off with a stream of nitrogen to give the titled methyl ester.

EXAMPLES 187–192

In the manner of Example 186 described above, the prostaglandins listed in Table VI are esterified with the indicated diazoalkanes.

added. After 1 hour, 45 minutes, a solution of 2.35 g (6.38 mmol) of 2-(6-carbotrimethylsilyloxyhex-2-cis-enyl) 4-trimethylsilyloxycyclopent-2-en-1-one in 35 ml of ether is added. After stirring for 1 hour at −78° C. and 1 hour at 0° C., the mixture is poured into dilute hydrochloric acid. The mixture is extracted with ether. The ether is removed and the residue is dissolved in 14 ml of acetic acid-tetrahydrofuran-water 4:2:1. After 1 hour the mixture is poured into water and extracted with ether. The ether is removed. The residue is purified by dry column chromatography on silica gel eluting with ether containing 0.75% acetic acid; 1.1 g of the subject compound is obtained.

EXAMPLES 195–208

By allowing the conjugate addition mixtures to warm to 0° C. in accordance with the methods described in

Table VI

| Example | Prostaglandin of Example | Diazoalkane | Product esterified prostaglandin |
|---|---|---|---|
| 187 | 71 | diazomethane | methyl nat-(and ent)-11α,16-dihydroxy-9-oxo-16,17-tetramethylene-18,19,20-trinor-5-cis-13-trans-prostadienoate |
| 188 | 74 | diazoethane | ethyl nat-(and ent-15R,16S)-11α,15-dihydroxy-9-oxo-15,16-trimethylene-13-trans-prostenoate |
| 189 | 75 | 1-diazopropane | n-propyl nat-15S,16S-(and ent-15R,16S)-11α,15-dihydroxy-9-oxo-15,16-trimethylene-13-trans-prostenoate |
| 190 | 76 | diazomethane | methyl-nat-(and ent)-11α,15-dihydroxy-9-oxo-15,16-tetramethylene-17,18,19,20-tetranor-13-trans-prostenoate |
| 191 | 118 | 1-diazohexane | n-hexyl-nat-15S,16R-(and ent-15R,16S)-11α,-15-dihydroxy-9-oxo-15,16-trimethylene-5-cis-13-trans-prostadienoate |
| 192 | 194 | diazoethane | ethyl-nat-(and ent)-15-hydroxy-9-oxo-15,16-tetramethylene-17,18,19,20-tetranor-5-cis-10,13-trans-prostatrienoate |

EXAMPLE 194

Preparation of nat-(and ent)-15-hydroxy-9-oxo-15,16-tetramethylene-17,18,19,20-tetranor-5-cis-10,13-trans-prostatrienoic Acid To 2.07 g (6.38 mmol) of 1-(2-iodovinyl)-1-trimethylsilyloxy cyclohexane in 3 ml of toluene is added with stirring under nitrogen at =40° C. 16.1 ml of 0.8 M t-butyllithium in pentane. After 1 hour, 6 ml of ether is added and the mixture is stirred at 25° C. for 25 minutes. The solution is cooled to −78° C. and a solution of 0.842 g (6.45 mmol) of copper pentyne and 2.58 ml of hexamethylphosphorous triamide in 35 ml of ether is Example 194 the products of Table VII are prepared from the indicated vinyl iodides or vinyl tin compound and the indicated cyclopent-2-en-1-one.

In those cases where two diastereoisomers are formed in the conjugate addition, only one of the diastereoisomers is listed in Table VII. It should be understood that the other diastereoisomer is also formed which in its nat and ent forms has an opposite (mirror image) configuration at the assymmetric carbon atoms on the β-chain (the chain containing $C_{13}$-$C_{14}$... etc.) to that of the respective nat and ent forms of the listed diastereoisomer; both of these diastereoisomers are claimed in the invention as well as their component enantiomers.

Table VII

| Example | Vinyl Iodide or Vinyl Tin of Example | Cyclopent-2-en-1-one | Product 9-oxo-10,13-trans-prosta-dienoic and its diastereoisomer where applicable (see hereinabove) |
|---|---|---|---|
| 195 | 29a | 2-(6-carboxyethyl)-4-hydroxycyclopent-2-en-1-one | nat-15S,16R-(and ent-15R,16S)-15-hydroxy-9-oxo-15,16-trimethylene-13-trans,10-prostadienoic acid |
| 196 | 36 | 2-(6-carboxyhexyl)-4-hydroxycyclopent-2-en-1-one | nat-15S,16S-(and ent-15R,16R)-15-hydroxy-9-oxo-15,16-trimethylene- |

Table VII-continued

| Example | Vinyl Iodide or Vinyl Tin of Example | Cyclopent-2-en-1-one | Product 9-oxo-10,13-trans-prostadienoic and its diastereoisomer where applicable (see hereinabove) |
|---|---|---|---|
| 197 | 31 | 2-(6-carboxyhexyl)-4-hydroxycyclopent-2-en-1-one | 13-trans,10-prostadienoic acid nat-(and ent)-15-hydroxy-9-oxo-15,16-tetramethylene-17,18,19,20-tetranor-13-trans,10-prostadienoic acid |
| 198 | 39 | 2-(6-carboxyhexyl)-4-hydroxycyclopent-2-en-1-one | nat-15R,16S-(and ent-15S,16R)-15-hydroxy-9-oxo-15,16-trimethylene-16-(3-trifluoromethylphenoxy)-17,18,-19,20-tetranor-13-trans,10-prostadienoic acid |
| 199 | 40 | 2-(6-carboxyhexyl)-4-hydroxycyclopent-2-en-1-one | nat-15R,16R,-(and ent-15S,16S)-15-hydroxy-9-oxo-15,16-trimethylene-16-(3-trifluoromethylphenoxy)-17,18,19,20-tetranor-13-trans,10-prostadienoic acid |
| 200 | 30 | 2-(6-carboxyhexyl)-4-hydroxycyclopent-2-en-1-one | nat-(and ent)-16-hydroxy-9-oxo-16,17-tetramethylene-18,19,20-trinor-13-trans,10-prostadienoic acid |
| 201 | 42 | 2-(5-carboxypentyl)cyclopent-2-en-1-one | nat-15R,16R-(and ent-15S,16S)-15-hydroxy-9-oxo-15,16-trimethylene-16-(4-fluorophenoxy)-17,18,19,20-21-pentanor-13-trans,10-prostadienoic acid |
| 202 | 29a | 2-(6-carboxyhex-2-cis-enyl)-4-hydroxycyclopent-2-en-1-one | nat-15S,16R-(and ent-15R,16S)-15-hydroxy-9-oxo-15,16-trimethylene-13-trans-5-cis,10-prostadienoic acid |
| 203 | 36 | 2-(6-carboxyhex-2-cis-enyl)-4-hydroxycyclopent-2-en-1-one | nat-15S,16S-(and ent-15R,16R)-15-hydroxy-9-oxo-15,16-trimethylene-13-trans-5-cis,10-prostatrienoic acid |
| 204 | 39 | 2-(6-carboxyhex-2-cis-enyl)-4-hydroxycyclopent-2-en-1-one | nat-15R,16S-(and ent-15S,16R)-15-hydroxy-9-oxo-15,16-trimethylene-16-(3-trifluoromethylphenoxy)-17,18,19,20-tetranor-13-trans-5-cis,10-prostatrienoic acid |
| 205 | 40 | 2-(6-carboxyhex-2-cis-enyl)-4-hydroxycyclopent-2-en-1-one | nat-15R,16R-(and ent-15S,16S)-15-hydroxy-9-oxo-15,16-trimethylene-16-(3-trifluoromethylphenoxy)-17,18,19,20-tetranor-13-trans-5-cis,10-prostatrienoic acid |
| 206 | 41 | 2-(6-carboxyhex-2-cis-enyl)-4-hydroxycyclopent-2-en-1-one | nat-15R,16S-(and ent-15S,16R)-15-hydroxy-9-oxo-15,16-trimethylene-16-(4-fluorophenoxy)-17,18,19,20-tetranor-13-trans-5-cis,10-prostatrienoic acid |
| 207 | 43 | 2-(6-carboxyhex-2-cis-enyl)-4-hydroxycyclopent-2-en-1-one | nat-15R,16S-(and ent-15S,16R)-15-hydroxy-9-oxo-15,16-trimethylene-16-(3-chlorophenoxy)-17,18,19,20-tetranor-13-trans-5-cis,10-prostatrienoic acid |
| 208 | 30 | 2-(6-carboxyhex-2-cis-enyl)-4-hydroxycyclopent-2-en-1-one | nat-(and ent)-16-hydroxy-9-oxo-16,-17-tetramethylene-18,19,20-trinor-13-trans-5-cis,10-prostatrienoic acid |

EXAMPLE 209

Preparation of nat-(and ent)-15-hydroxy-9-oxo-15,16-tetramethylene-17,18,19,20-tetranor-10,13-trans-prostadienoic acid A solution of 1.5 g of nat-(and ent)-11α,15-dihydroxy-9-oxo-15,16-tetramethylene-17,18,19,20-tetranor-13-trans-prostenoic acid 80 ml of 0.5N hydrochloric acid in 1:1 tetrahydrofuran-water is allowed to stand at room temperature under argon for 72 hours. The solution is treated with brine and extracted with ether. The extract is washed with brine and dried with anhydrous magnesium sulfate. The residue remaining after evaporation of the solvent is purified by dry column chromatography on silica gel to give the product as an oil.

EXAMPLE 210

Preparation of nat(and ent)-16-Hydroxy-9-oxo-16,17-tetramethylene-18,19,20-trinor-5-cis-10,13-trans-prostatrienoic Acid A 40 mg portion of nat(and ent)-11α,16-dihydroxy-9-oxo-16,17-tetramethylene-18,19,20-trinor-5-cis-13-trans-prostadienoic acid is dissolved in 5 ml of 0.5N hydrochloric acid in tetrahydrofuran-water (prepared by diluting 5 ml of 1N hydrochloric acid to 10 ml with tetrahydrofuran) with stirring under nitrogen at room temperature for 3 days. The mixture is poured into saturated sodium chloride solution and extracted with ether. The ether extract is washed with water and brine and the solvent is evaporated. The dried residue is spotted on a thin layer chromatography plate and developed with 40% ethyl acetate:0.5% acetic acid in hexane twice. The product is recovered in ethyl acetate.

EXAMPLES 211-225

Treatment of the 11α,9-oxo-prostenoic acids listed in Table VIII below with dilute acid in accordance with the method described in Examples 209 and 210 furnishes the products of the table.

EXAMPLES 228-233

In the mamner described above in Example 227 the 11α-hydroxy compounds listed in Table IX are treated with potassium carbonate to give the listed $\Delta^{8(12)}$ derivatives.

Table VIII

| Example | 11α-hydroxy-9-oxo-prostaglandin of Example | Product 9-oxo-10,13-trans-prostaglandin |
|---|---|---|
| 211 | 131 | nat-15R,16R-(and ent-15S,16S)-15-hydroxy-9-oxo-15,16-trimethylene-16-(3-chlorophenoxy)-17,18,19,20-tetranor-10,13-trans-5-cis-prostadienoic acid |
| 212 | 136 | nat-16R,17S-(and ent-16S,17R)-16-hydroxy-9-oxo-16,17-trimethylene-17-(3-trifluoromethylphenoxy)-18,19,20-trinor-10,13-trans-5-cis-prostadienoic acid |
| 213 | 137 | nat-16R,17R-(and ent-16S,17S)-16-hydroxy-9-oxo-16,17-trimethylene-17-(3-trifluoromethylphenoxy)-18,19,20-trinor-10,13-trans-5-cis-prostadienoic acid |
| 214 | 138 | nat-15S,16R-(and ent-15R,16S)-15-hydroxy-9-oxo-15,16-trimethylene-1a,1b-dihomo-10,13-trans-5-cis-prostadienoic acid |
| 215 | 140 | nat-(and ent-)-15-hydroxy-9-oxo-15,16-tetramethylene-1a,1b-dihomo-17,18,19,20-tetranor-10,13-trans-5-cis-prostdienoic acid |
| 216 | 146 | nat-15S,16S-(and ent-15R,16R)-15-hydroxy-9-oxo-3-oxa-15,16-trimethylene-10,13-trans-prostenoic acid. |
| 217 | 147 | nat-(and ent)-15-hydroxy-9-oxo-3-oxa-15,16-tetramethylene-17,18,19,20-tetranor-10,13-trans-prostenoic acid. |
| 218 | 151 | nat-15S,17S-(and ent-15R,17R)-15-hydroxy-9-oxo-4-methyl-15,17-trimethylene-19,20-dinor-10,13-trans-prostenoic acid. |
| 219 | 156 | nat-methyl-15S,16R-15-hydroxy-9-oxo-15,16-trimethylene-10,13-trans-prostenoate |
| 220 | 158 | nat-methyl-15-hydroxy-9-oxo-15,16-tetramethylene-17,18,19,20-tetranor-10,13-trans-prostenoate |
| 221 | 159 | nat-methyl-16-hydroxy-9-oxo-16,17-tetramethylene-18,19,20-trinor-10,13-trans-prostenoate |
| 222 | 163 | ent-methyl-15R,16R-15-hydroxy-9-oxo-15,16-trimethylene-10,13-trans-prostenoate |
| 223 | 168 | nat-methyl-15S,16R-15-hydroxy-9-oxo-15,16-trimethylene-10,13-trans-5-cis-prostadienoate |
| 224 | 172 | nat-methyl-15R,16S-15-hydroxy-9-oxo-15,16-trimethylene-16-(3-trifluoromethylphenoxy)-17,18,19,20-tetranor-10,13-trans-5-cis-prostadienoate |
| 225 | 173 | nat-methyl-15R,16R-15-hydroxy-9-oxo-15,16-trimethylene-16-(3-trifluoromethylphenoxy)-17,18,19,20-tetranor-10,13-trans-5-cis-prostadienoate |

EXAMPLE 227

Preparation of nat(and ent)-15-hydroxy-9-oxo-15,16-tetramethylene-17,18,19,20-tetranor-5-cis,8,13-trans-prostatrienoic acid A solution of 0.70 g of potassium carbonate and 0.40 g of nat(and ent)-11α,15-dihydroxy-9-oxo-15,16-tetramethylene-17,18,19,20-tetranor-5-cis-13-trans-prostadienoic acid in 200 ml of methanol-water 5:5 is allowed to stand at room temperature for 24 hours. The solution is diluted with water and acidified with hydrochloric acid. The solution is extracted with ether. The ether layer is dried over magnesium sulfate. The solvent is removed giving the titled compound as an oil.

EXAMPLE 234

Preparation of nat(and ent)-11α/βCyano-15-hydroxy-9-oxo-15,16-tetramethylene-17,18,19,20-tetranor-5-cis-13-trans-prostadienoic Acid A mixture of 0.45 g of nat(and ent)-15-hydroxy-9-oxo-15,16-tetramethylene-17,18,19,20-tetranor-13-trans,5-cis,10-prostatrienoic acid, 0.68 g of acetone cyanohydrin and 0.143 g of sodium carbonate in one ml of methanol and one ml of water is stirred at reflux under nitrogen for 2 hours. The solution is then stirred overnight. The resulting dark solution is diluted with water, acidified with HCL and extracted with ether. The ether solution is dried with MgSO₄ and activated charcoal and filtered through a pad of silica gel. The solvent is removed giving 0.37 g of the desired product.

EXAMPLES 235-243

In the manner described above for Example 234, the 11α/βcyano derivatives listed in Table X are prepared from the listed Δ$^{10}$ derivatives.

Table IX

| Example | 11α-hydroxy prostaglandin of Example | Δ$^{8(12)}$-prostaglandin |
|---|---|---|
| 228 | 71 | nat-(and ent)-16-hydroxy-9-oxo-16,17-tetramethylene-18,19,20-trinor-8,13-trans,5-cis-prostatrienoic acid |
| 229 | 74 | nat-15S,16R-(and ent-15R,16S)-15-hydroxy-9-oxo-15,16-trimethylene-8,13-trans-prostadienoic acid |
| 230 | 75 | nat-15S,16S-(and ent-15R,16R)-15-hydroxy-9-oxo-15,16-trimethylene-8,13-trans-prostadienoic acid |
| 231 | 76 | nat-(and ent)-15-hydroxy-9-oxo-15,16-tetramethylene-17,18,19,20-tetranor-8,13-trans-prostadienoic acid |
| 232 | 118 | nat-15S,16R-(and ent-15R,16S)-15-hydroxy-9-oxo-15,16-trimethylene-8,13-trans-5-cis-prostatrienoic acid |
| 233 | 119 | nat-15S,16S-(and ent-15R,16R)-15-hydroxy-9-oxo-15,16-trimethylene-8,13-trans,5-cis-prostatrienoic acid |

Table X

| Example | Δ$^{10}$ Derivative of Example | 11α/β Cyano prostaglandin |
|---|---|---|
| 235 | 195 | nat-15S,16R-(and ent-15R,16S)-11α/β-cyano-15-hydroxy-9-oxo-15,16-trimethylene-13-trans-prostenoic acid |
| 236 | 196 | nat-15S,16S-(and ent-15R,16R)-11α/β-cyano-15-hydroxy-9-oxo-15,16-trimethylene-13-trans-prostenoic acid |
| 237 | 197 | nat-(and ent)-11α/β-cyano-15-hydroxy-9-oxo-15,16-tetramethylene-17,18,19,20-tetranor-13-trans-prostenoic acid |
| 238 | 198 | nat-15R,16s-(and ent-15S,16R)-11α/β-cyano-15-hydroxy-9-oxo-15,16-trimethylene-16-(3-trifluoromethylphenoxy)-17,18,19,20-tetranor-13-trans-prostadienoic acid |
| 239 | 199 | nat-15R,16R-(and ent-15S,16S)-11α/β-cyano-15-hydroxy-9-oxo-15,16-trimethylene-16-(3-trifluoromethylphenoxy)-17,18,19,20-tetranor-13-trans-prostenoic acid |
| 240 | 200 | nat-(and ent)-11α/β-cyano-16-hydroxy-9-oxo-16,17-tetramethylene-18,19,20-trinor-13-trans-prostenoic acid |
| 241 | 210 | nat-(and ent)-11-α/β-cyano-16-hydroxy-9-oxo-16,17-tetramethylene-18,19,20-trinor-13-trans,5-cis-prostadienoic acid |
| 242 | 209 | nat-(and ent)-11α/β-cyano-15-hydroxy-9-oxo-15,16-tetramethylene-17,18,19,20-tetranor-13-trans-prostenoic acid |
| 243 | 213 | nat-16R,17R-(and ent-16S,17S)-11α/β-cyano-16-hydroxy-9-oxo-16,17-trimethylene-17-(3-trifluoromethylphenoxy)-18,19,20-trinor-13-trans-5-cis-prostenoic acid |

EXAMPLE 244

Preparation of 2-(6-Carbotrimethylsilyloxyhex-2-cis-enyl)-4-trimethylsilyloxycyclopent-2-en-1-one To a solution of one g of 2-(6-carboxyhex-2-cis-enyl)-4-hydroxycyclopent-2-en-1-one in 12.5 ml of dry pyridine at 15° C. under argon is added with stirring 3.3 ml of hexamethyldisilazane (HMDS) followed by dropwise addition of 1.6 ml of trimethylchlorosilane (TMCS). The resulting mixture is stirred at ambient temperature for one hour then taken to dryness (vac. pump). The residue is taken up in hexanes and filtered thru Celite. Evaporation of the mother liquor followed by two evaporations with toluene furnished 1.5 g (96%) of pure 2-(6-carbotrimethylsilyloxyhex-2-cis-enyl)-4-trimethylsilyloxycyclopent-2-en-1-one.

EXAMPLE 245

Preparation of 2-(6-Carbotrimethylsilyloxyhexyl)-4-trimethylsilyloxycyclopent-2-en-1-one To a solution of one g of 2-(6-carboxyhexyl)-4-hydroxycyclopent-2-en-1-one in 12.5 ml of dry pyridine at 15° C. under argon, is added with stirring 3.3 ml of hexamethyldisilazane followed by dropwise addition of 1.6 ml of trimethylchlorosilane. The resulting mixture is stirred at ambient temperature for one hour and then taken to dryness. The residue is taken up in hexane and filtered through diatomaceous earth. Evaporation of the mother liquor followed by two evaporations with toluene gives pure product.

EXAMPLE 246

Preparation of 2-(6-carbomethoxyhexyl)-4-trimethylsilyloxycyclopent-2-en-1-one

To a solution of 1.0 g of 2-(6-carbomethylhexyl)-4(R)-hydroxycyclopent-2-en-1-one [R. Pappo, et al., Tetrahedron Letters, 943 (1973)]in 12.5 ml of dry pyridine at 15°0 under argon was added with stirring 3.3 ml (24 mmoles) of hexamethyldisilazane (HMDS) followed by dropwise addition of 1.6 ml (20.5 mmoles) of trimethylchlorosilane (TMCS). The resulting mixture was stirred at ambient temperature for 1 hour then taken to dryness (vac. pump.). The residue is taken up in hexanes and filtered thru Celite. Evaporation of the mother liquor followed by two evaporations with toluene furnished 2-(6-carbomethoxyhexyl)-4(R)-trimethylsilyloxycyclopent-2-en-1-one.

EXAMPLE 247

Preparation of 2-(6-carbomethoxyhexyl)-4(S)-trimethylsilyloxycyclopent-2-en-1-one In the manner described in Example 239, treatment of 2-(6-carbomethoxyhexyl)-4-(S)-hydroxycyclopent-2-en-1-one [R.Pappo, et al., Tetrahedron Letters, 943 (1973)] with hexamethyldisilazane and trimethylsilylchloride gives the subject product.

EXAMPLE 248

Preparation of 5-chloro-1-(2-furyl)-1-pentanol

To a stirred suspension of 2-furyllithium (prepared from 0.53 moles of n-butyllithium and 39.5 g of furan by the procedure of *J. Org. Chem.*, 27, 1216 (1962) ) in 350 ml of ether and ca. 200 ml of hexane at −78° is added a solution of 57.9 g of 5-chloropentanol (*Chem. Abstr.*, 59, 7579F (1963) ) in 80 ml of ether during 25 minutes. The mixture is warmed to 0° during 20 minutes, stirred at 0° for 15 minutes, and treated with 140 ml of saturated ammonium chloride. The ether phase is washed with water and brine, dried over magnesium sulfate and potassium carbonate mixture, and concentrated to give a liquid, pmr spectrum (CDCl$_3$): $\delta$3.59 (triplet, C$\underline{H}_2$Cl$_2$) and 4.70 (triplet, CH$_2$C$\underline{H}$OH).

EXAMPLE 249

Preparation of 5-(carbethoxymethylthio)-1-(2-furyl)-1-pentanol

To a stirred, refluxing mixture of 76 g of ethyl mercaptoacetate, 79.5 g of 5-chloro-1-(2-furyl)-1-pentanol (Example 248 ), and 10 ml of 1.5M sodium ethoxide in ethanol is added an additionan 300 ml of 1.5M sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): $\delta$3.24 (singlet, —S—CH$_2$CO$_2$C$_2$H$_5$) and 4.70 (triplet, CH$_2$CHOH).

EXAMPLE 250

Preparation of 2-(6-carboxy-5-thiahexyl)-4-hydroxycyclopent-2-en-1-one stirred solution of 125 g of 5-(carbethoxymethylthio)-1-(2-furyl)-1-pentanol (Example 249), 22.4 g of sodium formate, 250 ml of formic acid, and 400 mg of hydroquinone in 2000 ml of dioxane and 1330 ml of water is refluxed for 20 hours.

The solution, containing crude 3-hydroxy-2-[4-(carbethoxymethylthio)butyl]cyclopent-4-en-1-one, is cooled and treated during 10 minutes with 75 ml of sulfuric acid (d=1.84) with stirring. The stirred solution is reluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil, pmr spectrum (CDCl$_3$):$\delta$3.24 (singlet, —S—CH$_2$—CO$_2$C$_2$H$_5$), 5.0 (broad singlet —CHOH—).

EXAMPLE 251

Preparation of 2-(6-carbotrimethylsilyloxy-5-thiahexyl)-4-trimethylsiloxycyclopent-2-en-1-one To a stirred solution of 28.4 g of 4-hydroxy-2-[4-(carboxymethylthio)butyl]cyclopent-2-en-1-one (Example 57) and 76 ml of hexamethyldisiliazane in 330 ml of pyridine at 5° is added 38 ml of chlorotrimethylsilane during 5 minutes. The mixture is stirred at ambient temperature for 3.5 hours, at 45° for 5 minutes, and then evaporated to remove solvent. The residue is stirred with 1000 ml of petroleum ether and filtered. The filtrate is treated with charcoal and filtered; this filtrate is concentrated with the aid of toluene to give a liquid, pmr spectrum (CDCl$_3$): $\delta$0.18 (singlet, trimethylsiloxy group) and 0.28 (singlet, trimethylsiloxycarbonyl group).

EXAMPLE 252

Preparation of 4-chloro-1-(2-furyl)-1-butanol

To a stirred suspension of 2-furyllithium (prepared from 0.53 moles of n-butyllithium and 39.5 g of furan by the procedure of *J. Org. Chem.*, 27, 1216 (1962)) in 350 ml of ether and ca. 200 ml of hexane at −78° is added a solution of 57.9 g of 4-chlorobutanol (*Chem. Abstr.*, 59, 7579F (1963)) in 80 ml of ether during 25 minutes. The mixture is warmed to 0° during 20 minutes, stirred at 0° for 15 minutes, and treated with 140 ml of saturated ammonium chloride. The ether phase is washed with water and brine, dried over magnesium sulfate and potassium carbonate mixture, and concentrated to give a liquid, pmr spectrum (CDCl$_3$):$\delta$3.59 (triplet, CH$_2$Cl) and 4.70 (triplet, CH$_2$CHOH).

EXAMPLE 253

Preparation of 4-carbethoxymethylthio)-1-(2-furyl)-1-butanol

To a stirred, refluxing mixture of 76 g of ethyl mercaptoacetate, 79.5 g of 4-chloro-1-(2-furyl)-1-butanol (Example 59), and 10 ml of 1.5M sodium ethoxide in ethanol is added an additional 300 ml of 1.5M sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): $\delta$3.24 (singlet, —S—CH$_2$—CO$_2$C$_2$H$_5$) and 4.70 (triplet, CH$_2$CHOH).

EXAMPLE 254

Preparation of 2-(5-carboxy-4-thiapentyl)-4-hydroxycyclopent-2-en-1-one

A stirred solution of 125 g of 4-(carbethoxymethylthio)-1-(2-furyl)-1-butanol (Example 60), 22.4 g of sodium formate, 250 ml of formic acid, and 400 mg of hydroquinone in 2000 ml of dioxane and 1330 ml of water is refluxed for 20 hours.

The solution, containing crude 3-hydroxy-2-[3-(carbethoxymethylthio)propyl]cyclopent-4-en-1-one, is cooled and treated during 10 minutes with 75 ml of sulfuric acid (d=1.84) with stirring. The stirred solution is refluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil.

EXAMPLE 255

Preparation of 2-(5-carbotrimethylsilyloxy-4-thiapentyl)-4-trimethylsiloxycyclopent-2-en-1-one To a stirred solution of 28.4 g of 4-hydroxy-2-[4-(carboxymethylthio)butyl]cyclopent-2-en-1-one (Example 57) and 76 ml of hexamethyldisilazane in 330 ml of pyridine at 5° is added 38 ml of chlorotrimethylsilane during 5 minutes. The mixture is stirred at ambient temperature for 3.5 hours, at 45° for 5 minutes, and then evaporated to remove solvent. The residue is slurried with 1000 ml of petroleum ether and filtered. The filtrate is treated with charcoal and filtered; this filtrate is concentrated with the aid of toluene to give a liquid, pmr spectrum $(CDCl_3)$:$\delta 0.18$ (singlet, trimethylsiloxy group) and 0.28 (singlet, trimethylsiloxycarbonyl group).

EXAMPLE 256

Preparation of nat(and ent)-11α,15-dihydroxy-9-oxo-15,16-tetramethylene-17,18,19,20-tetranor prostanoic acid A solution of nat(and ent)-11α,15-dihydroxy-9-oxo-15,16-tetramethylene-17,18,19,20-tetranor-13-trans-prostanoic acid (800 mg) in 50 ml of ethyl acetate is hydrogenated in a Parr apparatus using 500 mg of 5% rhodium-on-carbon. The catalyst is removed by filtration and the filtrate is taken to dryness to furnish of the titled product.

EXAMPLES 257–259

Hydrogenation of the prostenoic acids listed in Table XI below in ethyl acetate using a rhodium-on-carbon catalyst in accordance with the method described in Example 63 gives the prostanoic acids of the table.

Table XI

| Example | 13-trans-prostenoic acid of Example | Prostanoic Acid |
|---|---|---|
| 257 | 72 | nat-15S,16R-(and ent-15R,16S)-11α,15-dihydroxy-9-oxo-15,16-trimethylene prostanoic acid |
| 258 | 73 | nat-15S,16S-(and ent-15R,16R)-11α,15-dihydroxy-9-oxo-15,16-trimethylene prostanoic acid |
| 259 | 83 | nat-(and ent)-11α,16-dihydroxy-9-oxo-16,17-tetramethylene-18,19,20-trinor prostanoic acid |

We claim:
1. An optically active compound of the formula:

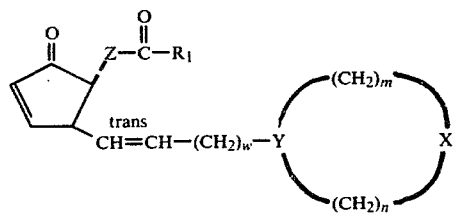

wherein $R_1$ is selected from the group consisting of hydroxy and $C_1$–$C_6$ alkoxy; Y is a trivalent radical selected from the group consisting of a moiety of the formula

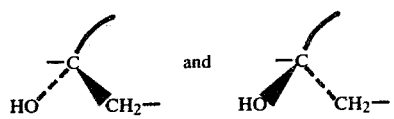

X is a divalent radical selected from the group consisting of a moiety of the formula

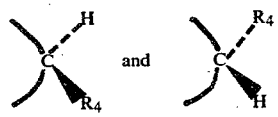

wherein $R_4$ is selected from the group consisting of $C_1$–$C_7$ alkyl, hydrogen; n is zero or an integer from 1 to 4; m is zero or an integer from 1 to 4, with the proviso that the sum of n and m has the value of 2 to 4; w is zero or 1; Z is a divalent radical selected from the group consisting of a moiety of the formula —$(CH_2)_p$—, —$(CH_2)_t$—O—$CH_2$—, and —$(CH_2)_t$—S—$CH_2$—, wherein p is an integer from 5 to 7, and t is an integer from 3 to 5; the racemic mixture thereof; the mirror image thereof; and the pharmacologically acceptable cationic salts thereof when $R_1$ is hydrogen.

2. The compound according to claim 1, wherein t is 4.
3. The compound according to claim 2, wherein p is 6.
4. The compound according to claim 3, wherein Z is —$(CH_2)_4$—O—$CH_2$—.
5. The compound according to claim 3 wherein Z is —$(CH_2)_4$—S—$CH_2$—.
6. The compound according to claim 3, wherein Z is —$(CH_2)_6$—.
7. The compound according to claim 6, wherein w is zero.
8. The compound according to claim 6, wherein w is one.
9. A compound according to claim 4, nat-15S-16S-(and ent-15R,16R)-15-hydroxy-9-oxo-3-oxa-15,16- trimethylene-10,13-trans-prostadienoic acid.
10. A compound according to claim 4, methyl nat-15S, 16S-(and ent-15R,16R)-15-hydroxy-9-oxo-3-oxa-15,16-trimethylene-10,13-trans-prostadienoate.
11. A compound according to claim 4, nat-(and ent)-15-hydroxy-9-oxo-3-oxa-15,16-trimethylene-17,18,19,20-tetranor-10,13-trans-prostadienoic acid.
12. A compound according to claim 7, nat-15S,16R-(and ent-15R,16S)-15-hydroxy-9-oxo-15,16-trimethylene-10,13-trans-prostadienoic acid.
13. A compound according to claim 7, nat-15S,16R-15-hydroxy-9-oxo-15,16-trimethylene-10,13-trans-prostadienoic acid.

14. A compound according to claim 7, methyl nat-15S,16R-(and ent-15R,16S)-15-hydroxy-9-oxo-15,16-trimethylene-10,13-trans-prostadienoate.

15. A compound according to claim 7, methyl nat-15S,16R-15-hydroxy-9-oxo-15,16-trimethylene-10,13-trans-prostadienoate.

16. A compound according to claim 7, nat-15S,16S-(and ent-15R,16R)-15-hydroxy-9-oxo-15,16-trimethylene-10,13-trans-prostadienoic acid.

17. A compound according to claim 7, nat-15S,16S-15-hydroxy-9-oxo-15,16-trimethylene-10,13-trans-prostadienoic acid.

18. A compound according to claim 7, methyl nat-15S,16S-(and ent 15R,16R)-15-hydroxy-9-oxo-15,16-trimethylene-10,13-trans-prostadienoate.

19. A compound according to claim 7, methyl nat-15S,16S-15-hydroxy-9-oxo-15,16-trimethylene-10,13-trans-prostadienoate.

20. A compound according to claim 7, nat-(and ent)-15-hydroxy-9-oxo-15,16-tetramethylene-17,18,19,20-tetranor-10,13-trans-prostadienoic acid.

21. A compound according to claim 7, nat-15-hydroxy-9-oxo-15,16-tetramethylene-17,18,19,20-tetranor-10,13-trans-prostadienoic acid.

22. A compound according to claim 7, methyl nat-(and ent)-15-hydroxy-9-oxo-15,16-tetramethylene-17,18,19,20-tetranor-10,13-trans-prostadienoate.

23. A compound according to claim 7, methyl nat-15-hydroxy-9-oxo-15,16-tetramethylene-17,18,19,20-tetranor-10,13-trans-prostadienoate.

24. A compound according to claim 7, nat-(and ent)-15-hydroxy-9-oxo-15,16-trimethylene-17,18,19,20-tetranor-10,13-trans-prostadienoic acid.

25. A compound according to claim 7, nat-15-hydroxy-9-oxo-15,16-trimethylene-17,18,19,20-tetranor-10,13-trans-prostadienoic acid.

26. A compound according to claim 7, nat-(and ent)-15-hydroxy-9-oxo-15,16-pentamethylene-17,18,19,20-tetranor-10,13-trans-prostadienoic acid.

27. A compound according to claim 7, nat-15-hydroxy-9-oxo-15,16-pentamethylene-17,18,19,20-tetranor-10,13-trans-prostadienoic acid.

28. A compound according to claim 7, nat-15S,17R-(and ent-15R,17S)-15-hydroxy-9-oxo-15,17-dimethylene-10,13-trans-prostadienoic acid.

29. A compound according to claim 7, nat-15S,17R-15-hydroxy-9-oxo-15,17-dimethylene-10,13-trans-prostadienoic acid.

30. A compound according to claim 7, nat-15S,17S-(and-ent- 15R,17R)-15-hydroxy-9-oxo-15,17-dimethylene-10,13-trans-prostadienoic acid.

31. A compound according to claim 7, nat-15S,17S-15-hydroxy-9-oxo-15,17- dimethylene-10,13-trans-prostadienoic acid.

32. A compound according to claim 7, nat-15S,17R-(and ent-15R,17S)-15-hydroxy-9-oxo-15,17-trimethylene-19,20-dinor-10,13-trans-prostadienoic acid.

33. A compound according to claim 7, nat-15S,17R-15-hydroxy-9-oxo-15,17-trimethylene-19,20-dinor-10,13-trans-prostadienoic acid.

34. A compound according to claim 7, nat-15S,17S-(and ent-15R,17R)-15-hydroxy-9-oxo-15,17-trimethylene-19,20-dinor-10,13-trans-prostadienoic acid.

35. A compound according to claim 7, nat-15S,17S-15-hydroxy-9-oxo-15,17-trimethylene-19,20-dinor-10,13-trans prostadienoic acid.

36. A compound according to claim 7, nat-15S,16R-(and ent-15R,16S)-15-hydroxy-9-oxo-15,16-tetramethylene-10,13-trans-prostadienoic acid.

37. A compound according to claim 7, nat-15S,16R-15-hydroxy-9-oxo-15,16-tetramethylene-10,13-trans-prostadienoic acid.

38. A compound according to claim 7, nat-15S,16S-(and ent-15R,16R)-15-hydroxy-9-oxo-15,16-tetramethylene-10,13-trans-prostadienoic acid.

39. A compound according to claim 7, nat-15S,16S-15-hydroxy-9-oxo-15,16-tetramethylene-10,13-trans-prostadienoic acid.

40. A compound according to claim 8, nat-(and ent)-16-hydroxy-9-oxo-16,17-tetramethylene-18,19,20-trinor-10,13-trans-prostadienoic acid.

41. A compound according to claim 8, nat-16-hydroxy-9-oxo-16,17-tetramethylene-18,19,20-trinor-10,13-trans-prostadienoic acid.

42. A compound according to claim 8, methyl nat-(and ent)-16-hydroxy-9-oxo-16,17-tetramethylene-18,19,20-trinor-10,13-trans-prostadienoate.

43. A compound according to claim 8, methyl nat-16-hydroxy-9-oxo-16,17-tetramethylene-18,19,20-trinor-10,13-trans-prostadienoate.

44. A compound according to claim 8, nat-16R,17S-(and ent-16S,17R)-16-hydroxy-9-oxo-16,17-trimethylene-20-methyl-10,13-trans-prostadienoic acid.

45. A compound according to claim 8, nat-16R,17S-16-hydroxy-9-oxo-16,17-trimethylene-20-methyl-10,13-trans-prostadienoic acid.

46. A compound according to claim 8, nat-16R,17R-(and ent-16S,17S)-16-hydroxy-9-oxo-16,17-trimethylene-20-methyl-10,13-trans-prostadienoic acid.

47. A compound according to claim 8, nat-16R,17R-16-hydroxy-9-oxo-16,17-trimethylene-20-methyl-10,13-trans-prostadienoic acid.

* * * * *